(12) United States Patent
Aneja et al.

(10) Patent No.: US 12,245,746 B2
(45) Date of Patent: *Mar. 11, 2025

(54) DEVICES, SYSTEMS, AND METHODS FOR A BIOPSY CAP AND HOUSING

(71) Applicant: BOSTON SCIENTIFIC MEDICAL DEVICE LIMITED, Galway (IE)

(72) Inventors: Harchetan Singh Aneja, Amritsar (IN); Amit Sharad Bharos, Jabalpur (IN); Swami Upadhyay, Raipur (IN); Boopathi Rajarathnam, Salem (IN); Shalin Singh Rawat, Rishikesh (IN); Venkatesh Neelamegam, Tirupur (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 505 days.

This patent is subject to a terminal disclaimer.

(21) Appl. No.: 16/671,805

(22) Filed: Nov. 1, 2019

(65) Prior Publication Data

US 2020/0138272 A1 May 7, 2020

Related U.S. Application Data

(60) Provisional application No. 62/834,192, filed on Apr. 15, 2019, provisional application No. 62/834,201, (Continued)

(51) Int. Cl.
*A61B 1/00* (2006.01)
*A61B 1/015* (2006.01)
(Continued)

(52) U.S. Cl.
CPC ...... *A61B 1/00137* (2013.01); *A61B 1/00064* (2013.01); *A61B 1/0011* (2013.01);
(Continued)

(58) Field of Classification Search
CPC .............. A61B 1/00137; A61B 1/0014; A61B 1/00128; A61B 1/018; A61B 1/0011; A61B 1/015
See application file for complete search history.

(56) References Cited

U.S. PATENT DOCUMENTS 5,743,884 A 4/1998 Hasson et al.
5,993,379 A * 11/1999 Ouchi .................... A61B 46/10
600/154

(Continued)

FOREIGN PATENT DOCUMENTS

EP 1997444 A2 12/2008
EP 2505119 A1 10/2012
(Continued)

OTHER PUBLICATIONS

International Search Report and Written Opinion for International application No. PCT/IB2019/059409, mailed on Feb. 13, 2020, 11 pages.

(Continued)

*Primary Examiner* — Timothy J Neal
(74) *Attorney, Agent, or Firm* — Seager, Tufte & Wickhem, LLP

(57) ABSTRACT

The present disclosure relates generally to the field of medical instruments. More particularly, the present disclosure pertains to medical instruments for use with an endoscope, such as a biopsy cap and a biopsy cap housing with improved stability and stress distribution, for example, to securely attach to an endoscope biopsy port.

20 Claims, 18 Drawing Sheets

Related U.S. Application Data filed on Apr. 15, 2019, provisional application No. 62/768,808, filed on Nov. 16, 2018, provisional application No. 62/755,024, filed on Nov. 2, 2018.

(51) Int. Cl.
| | | |
|---|---|---|
| *A61B 1/018* | (2006.01) | |
| *A61B 10/02* | (2006.01) | |
| *A61B 10/04* | (2006.01) | |
| *B29D 99/00* | (2010.01) | |

(52) U.S. Cl.
CPC ........ *A61B 1/0014* (2013.01); *A61B 1/00147* (2013.01); *A61B 1/015* (2013.01); *A61B 1/018* (2013.01); *A61B 10/0275* (2013.01); *A61B 10/04* (2013.01); *B29D 99/0053* (2013.01)

(56) References Cited

U.S. PATENT DOCUMENTS

| | | | |
|---|---|---|---|
| 6,254,529 B1 * | 7/2001 | Ouchi ................ | A61B 1/018 604/167.03 |
| 6,606,515 B1 * | 8/2003 | Windheuser .... | A61M 25/09041 600/585 |
| 6,893,393 B2 | 5/2005 | Carrillo | |
| 8,388,521 B2 | 3/2013 | Byers et al. | |
| 8,434,041 B2 * | 4/2013 | Chen .................. | H01L 24/05 716/132 |
| 8,480,570 B2 | 7/2013 | Tinkham et al. | |
| 2005/0090835 A1 * | 4/2005 | Deal ................. | A61B 1/00137 606/1 |
| 2005/0171402 A1 | 8/2005 | Cohen et al. | |
| 2006/0195117 A1 | 8/2006 | Rucker et al. | |
| 2009/0005799 A1 | 1/2009 | Franer et al. | |
| 2009/0088600 A1 | 4/2009 | Meloul | |
| 2009/0287052 A1 | 11/2009 | Amos et al. | |
| 2009/0287111 A1 * | 11/2009 | Kaye ................. | A61B 1/00137 600/101 |
| 2010/0081878 A1 | 4/2010 | Byers et al. | |
| 2010/0087705 A1 | 4/2010 | Byers et al. | |
| 2010/0087710 A1 * | 4/2010 | Weldon ............. | A61B 1/00137 600/123 |
| 2012/0071713 A1 | 3/2012 | Kaye et al. | |
| 2012/0253128 A1 * | 10/2012 | Yamane ............ | A61B 1/00062 600/154 |
| 2016/0206859 A1 * | 7/2016 | Eden ................. | A61B 1/00121 |
| 2018/0014717 A1 * | 1/2018 | Benn ................. | A61B 1/00121 |
| 2018/0310806 A1 | 11/2018 | Gavalis et al. | |
| 2020/0138419 A1 * | 5/2020 | Aneja ............... | A61B 1/00064 |

FOREIGN PATENT DOCUMENTS

| | | |
|---|---|---|
| JP | S6129703 U | 2/1986 |
| JP | H10-57302 A | 3/1998 |
| JP | 2005080867 A | 3/2005 |
| JP | 2008529723 A | 8/2008 |
| WO | 2005011791 A2 | 2/2005 |
| WO | 2009143129 A1 | 11/2009 |
| WO | 2009143137 A1 | 11/2009 |
| WO | 2018024109 A1 | 2/2018 |

OTHER PUBLICATIONS

International Search Report and Written Opinion for International application No. PCT/IB2019/059408, mailed on Feb. 14, 2020, 12 pages.

International Search Report and Written Opinion for International application No. PCT/IB2019/059407, mailed on Feb. 14, 2020, 11 pages.

International Search Report and Written Opinion for International application No. PCT/IB2019/059413, mailed on Feb. 17, 2020, 10 pages.

International Search Report and Written Opinion for International application No. PCT/IB2019/059404, mailed on Feb. 17, 2020, 10 pages.

* cited by examiner

DEVICES, SYSTEMS, AND METHODS FOR A BIOPSY CAP AND HOUSING

PRIORITY

This application claims the benefit of priority under 35 USC § 119 to U.S. Provisional Patent Application Ser. No. 62/755,024, filed Nov. 2, 2018 and titled "Attachments for Endoscopes," U.S. Provisional Patent Application Ser. No. 62/768,808, filed Nov. 16, 2018 and titled "Internal Seal for Biopsy Cap," U.S. Provisional Patent Application Ser. No. 62/834,192, filed Apr. 15, 2019 and titled "Biopsy Cap and Biopsy Cap Housing," and to U.S. Provisional Patent Application Ser. No. 62/834,201, filed Apr. 15, 2019 and titled "Devices, Systems, and Methods For Providing Sealable Access To A Working Channel," the disclosures of which are incorporated by reference herein in their entirety and for all purposes.

FIELD

The present disclosure relates generally to the field of medical instruments. More particularly, the present disclosure pertains to medical instruments for use with an endoscope, such as a biopsy cap and a biopsy cap housing with improved stability and stress distribution, for example, to securely attach to an endoscope biopsy port.

BACKGROUND

A wide variety of medical instruments have been developed for medical use. Some of these devices include guidewires, guide tubes, catheters, endoscopes, endoscopic devices, and the like. These devices are manufactured by any one of a variety of different manufacturing methods and may be used according to any one of a variety of methods.

Some endoscope biopsy cap housings and biopsy caps can include a variety of deficiencies which may contribute—both individually and cumulatively—to component breakage, unnecessarily complicated or additional procedural steps and/or prolonged procedure times.

A variety of advantageous medical outcomes may therefore be realized by the biopsy cap and biopsy cap housing embodiments of the present disclosure.

SUMMARY

In an embodiment, a housing attachment for a biopsy port of an endoscope may include a first center-split half having a first portion defining a first half of an upper chamber. A second portion may define a first half of a lower chamber. A first locking member may extend from an inner surface of the first center-split half, the first locking member configured to engage the biopsy port. A second center-split half may include a first portion defining a second half of the upper chamber. A second portion may define a second half of the lower chamber. A second locking member may extend from an inner surface of the second center-split half, the second locking member configured to engage the biopsy port. Mating surfaces of the first and second center-split halves may be configured to interlock.

In various embodiments described here or otherwise, the upper chamber may be configured to receive a biopsy cap, and the lower chamber may be configured to receive the biopsy port. The first center-split half and the second center-split half may each comprise a substantially radially raised portion configured to engage corresponding recessed portions formed within an outer wall of a biopsy cap. A base may be disposed about the biopsy port and disposed within the biopsy cap. A first locking hook may be attached to a proximal end of the first center-split half, and a second locking hook attached to a proximal end of the second center-split half, wherein the first and second locking hooks are substantially adjacent to each other when the first and second center-split halves are interlocked. The first locking member and second locking member may each be angled radially inward and toward a direction of the upper chamber. At least one stabilizing member may extend from the inner surface of the first center-split half or the second center-split half, the at least one stabilizing member configured collide with the first locking member or second locking member upon a radial deformation of the first locking member or second locking member. At least one stabilizing member may include a perpendicular surface that is substantially perpendicular to the radial flexure of the first locking member or second locking member. At least one stabilizing member may be positioned such that the first locking member or second locking member may radially deform a maximum of about 15° to about 25°. The mating surface of the first center-split half may include one or more projections, and the mating surface of the second center-split half includes one or more receiving elements, and wherein the projections are configured to be received within corresponding receiving elements.

In an embodiment, a biopsy cap assembly may include a first center-split housing half including a first portion defining a first half of an upper chamber. A second portion may define a first half of a lower chamber. A second center-split housing half may include a first portion defining a second half of the upper chamber. A second portion may define a second half of the lower chamber. Mating surfaces of the first and second center-split housing halves may be configured to interlock to define the upper and lower chambers. A biopsy cap may be disposed within the upper chamber.

In various embodiments described here or otherwise, an outer wall of the biopsy cap includes recessed portions formed therein, and wherein the first center-split half and the second center-split half each comprise a substantially radially raised portion configured to engage corresponding recessed portions formed within an outer wall of a biopsy cap. A base may be disposed about the biopsy port and disposed within the biopsy cap. The housing may include a lip extending into a proximal end of the upper chamber and the biopsy cap includes a wedge extending outward from a top surface of the cap, and wherein the lip is configured to engage the top surface of the wedge. The housing may include a wedge formed within the inner surfaces of the first and second portions of the first and second center-split housing halves, and the biopsy cap may include a wedge extending outward from an outer wall of the biopsy cap top, wherein the wedge of the housing is configured to engage the wedge of the biopsy cap.

In an embodiment, a housing attachment for a biopsy port of an endoscope may include a body including an upper chamber configured to accept a biopsy cap. A lower chamber may be adjacent the upper chamber and configured to engage the biopsy port. A skirt region may be configured to accept a portion of the endoscope. The skirt region may include internal gripping members along an inner surface of the skirt region configured to frictionally fit with the portion of the endoscope. The upper chamber may include a substantially radially raised portion configured to engage corresponding recessed portions formed within an outer wall of a biopsy cap. A grip region may be about an external surface of the body at the upper chamber, the grip region comprising external gripping members configured for a user to grasp. At least two slots may extend through the body along the upper chamber and the skirt, the at least two slots configured to allow the body to flex upon compressing the grip region.

This disclosure provides design, material, manufacturing method, and use alternatives for medical instruments. Embodiments of an attachment for an endoscope are disclosed. The attachments may comprise one or more, or all of the features of: a housing; one or more angled locking members extending from an inner surface of the housing, the angled locking members being designed to engage a biopsy port of an endoscope; one or more stabilizing members extending from the inner surface of the housing; a locking apparatus coupled to the housing; and a biopsy cap disposed within the housing.

In various embodiments described herein, the one or more angled locking members may include a first angled locking member disposed on a first side of the inner surface of the housing and a second angled locking member disposed on a second side of the inner surface of the housing. The one or more angled locking members may include a first angled locking member and wherein the first angled locking member includes a bent region. The one or more angled locking members may include a first angled locking member and wherein the first angled locking member is substantially V-shaped. The one or more angled locking members may include a first angled locking member and wherein the first angled locking member is substantially rigid. The one or more angled locking members may include a first angled locking member and the first angled locking member may be resiliently deflectable. The one or more stabilizing members may include a first stabilizing member disposed on a first side of the inner surface of the housing and a second stabilizing member disposed on a second side of the inner surface of the housing. The one or more stabilizing members may include a first stabilizing member and wherein the first stabilizing member extends radially inward from the inner surface of the housing. The housing may include a skirt region. The locking apparatus may include one or more guidewire locks. The biopsy cap may include various sealing members, such as a resilient seal.

In an embodiment, an attachment for an endoscope is disclosed. The attachment may comprise one or more, or all of the features of: a housing designed to engage a biopsy port of an endoscope; a skirt region defined along a first end region of the housing; a locking region defined along a second end region of the housing; an angled locking member extending from an inner surface of the housing; a stabilizing member extending from the inner surface of the housing and disposed adjacent to the angled locking member; and a disposed within the housing.

In various embodiments, the housing may further comprise a second angled locking member extending from the inner surface of the housing and disposed opposite the angled locking member. The angled locking member may include a bent region. The angled locking member may be substantially V-shaped. The angled locking member may be substantially rigid. The angled locking member may be resiliently deflectable. A second stabilizing member may extend from the inner surface of the housing and disposed opposite the stabilizing member. The stabilizing member may extend radially inward from the inner surface of the housing.

In an embodiment, an attachment for an endoscope is disclosed. The attachment may comprise one or more, or all of the features of: a housing designed to engage a biopsy port of an endoscope; an asymmetrical skirt region defined along a first end region of the housing; a guidewire locking region defined along a second end region of the housing; a pair of angled locking members extending from an inner surface of the housing; a pair of stabilizing members extending from the inner surface of the housing and disposed adjacent to the pair of angled locking members; and a biopsy cap disposed within the housing, the biopsy cap including a resilient seal member.

In one aspect, the present disclosure relates to a biopsy cap housing comprising a first center-split half and a second center-split half. The first center-split half may include a first portion defining a first half of an upper chamber and a second portion defining a first half of a lower chamber. A first pivot member may be integrally formed with the first portion of the first center-split half. A first slit may extend through a sidewall of the first and second portions of the first center-split half and in substantial alignment with the first pivot member. The second center-split half may include a first portion defining a second half of the upper chamber and a second portion defining a second half the lower chamber. A second pivot member may be integrally formed with the first portion of the second center-split half. A second slit may extend through a sidewall of the first and second portions of the second center-split half and in substantial alignment with the second pivot member. Mating surfaces of the first and second center-split halves may be configured to interlock to define the upper and lower chambers.

In the described and other embodiments within the scope of the present disclosure, an elevated surface of the first pivot member may extend into the upper chamber and an elevated surface of the second pivot member may extend into the upper chamber substantially opposite the first pivot member. The upper chamber may be configured to receive a biopsy cap. The lower chamber may be configured to receive an endoscope biopsy port. The first and second pivot members may include a thickness greater than a wall thickness of the first and second center-split halves. A force applied to the first portions of the first and second center-split halves may move the second portions of the first and second center-split halves away from each other. A force applied to the second portions of the first and second center-split halves may move the first portions of the first and second center-split halves away from each other. The elevated surfaces of the first and second pivot members may be configured to engage a corresponding recessed portion formed within an outer wall of a biopsy cap disposed within the upper chamber. A first locking hook may be attached to a proximal end of the first center-split half and a second locking hook may attached to a proximal end of the second center-split half. The first and second locking hooks may be substantially adjacent to each other when the first and second center-split halves are interlocked. An inner surface of the first portions of the first and second center-split halves may include a surface feature configured to engage a corresponding surface feature formed on or within an outer wall of a biopsy cap disposed within the upper chamber. The surface feature of the housing may include a lip extending into a proximal end of the upper chamber. The surface feature of the biopsy cap may include a wedge extending inward from a top surface of the biopsy cap. The lip may be configured to engage the top surface of the wedge of the biopsy cap. The surface feature of the housing may include a wedge formed within the inner surfaces of the first and second portions of the first and second center-split halves. The surface feature of the biopsy cap may include a wedge extending outward from an outer wall of the biopsy cap top. The wedge of the housing may be configured to engage the wedge of the biopsy cap. The mating surface of the first center-split half may include one or more projections and the mating surface of the second center-split half may include one or more receiving elements. The projections may be configured to be received within corresponding receiving elements. The one or more projections may include one or more pins and the one or more receiving elements may include one or more pin holes. The one or more pins and corresponding one or more pin holes may be located at a proximal end of the first portions of the first and second center-split halves. The one or more pins and corresponding one or more pin holes may be located at a proximal end of the second portions of the first and second center-split halves. The one or more projections may include one or more pegs and the one or more receiving elements may include one or more sockets. The one or more pegs and corresponding one or more sockets may be located at a proximal end of the second portions of the first and second center-split halves. The one or more projections may include one or more snap-locks and the one or more receiving elements may include one or more snap-lock receivers. The one or more snap-locks and corresponding one or more snap-lock receivers may be located at a proximal end of the first portions of the first and second center-split halves. The one or more snap-locks and corresponding one or more snap-lock receivers may be located at a proximal end of the second portions of the first and second center-split halves. The one or more snap-locks may include an angled surface configured to positively engage a corresponding angled surface of the one or more snap-lock receivers. An inner surface of the second portions of the first and second center-split halves may include one or more locking members extending into the lower chamber and configured to releasably engage an outer surface of an endoscope biopsy port disposed within the lower chamber. An inner surface of the second portions of the first and second center-split halves may include one or more platforms extending into the lower chamber on opposite sides of the first and second slits and between the one or more locking members. An end of the one or more locking members and a surface of the one or more platforms may be separated by a distance within the lower chamber when a force is not applied to the first portions of the first and second center-split halves. An end of the one or more locking members and a surface of the one or more platforms may be in contact when a force is applied to the first portions of the first and second center-split halves. The force applied to the first portions of the first and second center-split halves may be an inward compressive force configured to move the second portions of the first and second center-split halves away from each other. The contact between the one or more locking members and the surface of the one or more platforms may prevent at least one of the locking members from breaking due to over-extension.

In one aspect, the present disclosure relates to a biopsy cap comprising one or more surface features formed on or within the biopsy cap. The one or more surface features may be configured to frictionally and/or compressingly engage a corresponding surface feature formed on or within an inner surface of a first portion of first and second center-split halves of a biopsy cap housing. The biopsy cap may include a first surface feature attached to or integrally formed with a proximal end of the biopsy cap and second and third surface features attached to or integrally formed with an outer wall of the biopsy cap. The one or more surface features may include first and second recessed portions integrally formed within an outer wall of the biopsy cap and separated from the second and third surface features by approximately 90-degrees relative to an outer circumference of the biopsy cap. The biopsy cap may be formed from or otherwise include a variety of compressible materials (e.g., silicone, rubbers, etc.) formed as a single unitary structure using. The surface feature may include a substantially contiguous lip. The surface feature may include substantially contiguous wedges. The surface feature may include recessed portions.

In one aspect, the present disclosure relates to a biopsy cap assembly comprising a first center-split housing half and a second center-split housing half. The first center-split half may include a first portion defining a first half of an upper chamber and a second portion defining a first half of a lower chamber. A first pivot member may be integrally formed with the first portion of the first center-split half. The second center-split half may include a first portion defining a second half of the upper chamber and a second portion defining a second half the lower chamber. A second pivot member may be integrally formed with the first portion of the second center-split half. Mating surfaces of the first and second center-split housing halves may be configured to interlock to define the upper and lower chambers. A biopsy cap may be disposed within the upper chamber.

In the described and other embodiments within the scope of the present disclosure, an outer wall of the biopsy cap may include recessed portions formed therein. An elevated surface of the first pivot member may extend into the upper chamber and an elevated surface of the second pivot member may extend into the upper chamber substantially opposite the first pivot member. The elevated surfaces may frictionally engage the recessed portions of the biopsy cap. The first and second pivot members may include a thickness greater than a wall thickness of the first and second center-split housing halves. The housing may include a lip extending into a proximal end of the upper chamber and the biopsy cap may include a wedge extending outward from a top surface of the cap. The lip may be configured to engage the top surface of the wedge. The housing may include a wedge formed within the inner surfaces of the first and second portions of the first and second center-split housing halves. The biopsy cap may include a wedge extending outward from an outer wall of the biopsy cap top. The wedge of the housing may be configured to engage the wedge of the biopsy cap.

The above summary of certain embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

DETAILED DESCRIPTION

Figure 1:
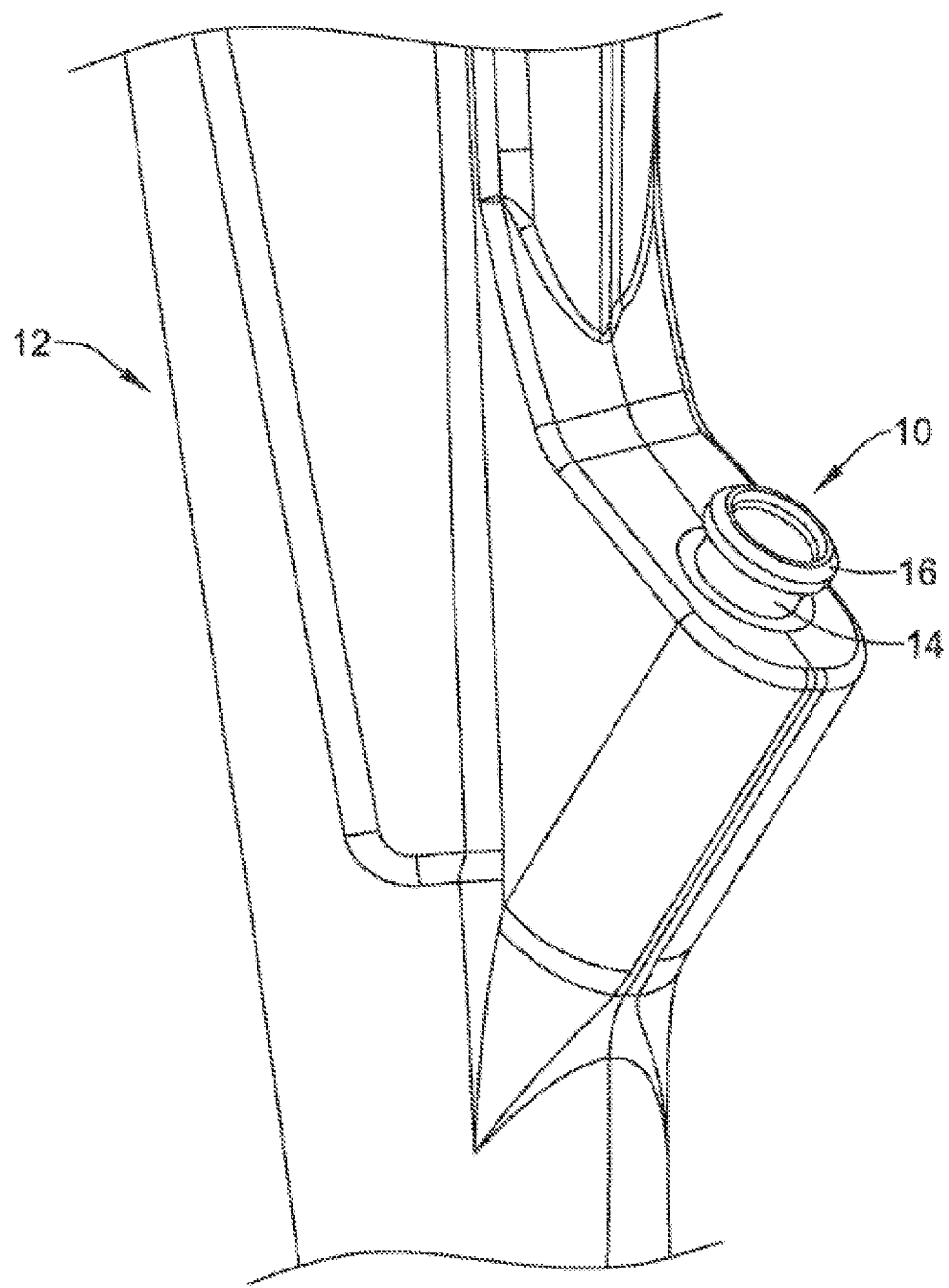
FIG. 1 is a plan view of a portion of an endoscope including a biopsy port to a working channel of the endoscope.

The present disclosure is not limited to the particular embodiments described herein. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Although embodiments of the present disclosure are described with specific reference to biopsy caps and biopsy cap housings configured to allow the delivery and/or exchange of a variety of medical instruments through the biopsy cap and port of an endoscope, laparoscope, or other visualization systems such as the Spy Glass™ Direct Visualization System (Boston Scientific Corp., Marlborough, MA), it should be appreciated that such designs may be adapted to fit and/or be used with a variety of medical instruments and medical applications which include sealable access.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Some biopsy cap housings tend to permit axial and rotational movement of the housing and/or cap during device exchange. In addition, exchange of larger diameter medical instruments (e.g., catheters, stent introducers, etc.) through the biopsy cap tends to exert a radially outward force which may cause the two center-split halves of some biopsy cap housings to partially or completely separate/disengage from each other. Adhesives applied to the center-split halves may minimize such separation but result in increased assembly time and cost. Locking or unlocking a guidewire to the hook(s) located on one side of a biopsy cap housing tends to exert a radially outward force on one of the center-split halves, which may cause the center-split halves to move in opposite directions and partially or completely separate/disengage from each other. Excessive flexing due to lateral forces applied to one or both center-split halves, e.g., during disengagement of the biopsy cap housing from the biopsy port, may concentrate stress on the locks which secure the biopsy cap housing to the endoscope port, resulting in a fracture of one or more of the locks. Any fracturing of components or separation between the center-split halves resulting from these forces may result in compromised stability between the biopsy cap housing and the endoscope biopsy port. In addition, the cumulative effects of these separation forces may decrease the operational longevity of the biopsy cap housing.

In various embodiments, features and advantages of providing sealable access to a working channel, e.g., of an endoscope, may be realized in combination with a biopsy cap and biopsy cap housing. Such sealable access to a working channel, which may be reinforced, may be implemented with features throughout the disclosures of U.S. patent application Ser. No. 16/100,960, filed Aug. 10, 2018 and titled "Biopsy Cap For Use With Endoscope,", U.S. Patent Publication No. 2020/0138274, published on May 7, 2020, and titled "Attachments For Endoscopes"; U.S. Patent Application Publication No. 2020/0138419, published on May 7, 2020, and issued as U.S. Pat. No. 11,690,499, on Jul. 4, 2023, and titled "Biopsy Cap And Biopsy Cap Housing"; U.S. Patent Application Publication No. 2020/0138277, published on May 7, 2020, and issued as U.S. Pat. No. 12,070,187, on Aug. 27, 2024, and titled, "Devices, Systems, And Methods For Providing Sealable Access To A Working Channel"; U.S. Patent Application Publication No. 2020/0138273, published on May 7, 2020, issued as U.S. Pat. No. 11,771,307, issued on Oct. 3, 2023, and titled "Internal Seal for Biopsy Cap"; U.S. Patent Application Publication No. 2020/0138276, published on May 7, 2020, issued as U.S. Pat. No. 11,478,223, on Oct. 25, 2022, and and titled "Devices, Systems, and Methods for Providing Sealable Access to a Working Channel," which are each incorporated by reference in their entirety and for all purposes.

During endoscopic procedures, a medical instrument such as a guidewire, catheter, endoscopic instrument, or the like may be inserted through a working channel of the endoscope. A port (e.g., a "biopsy port") along the endoscope may provide access to the working channel. During use, it may be desirable to couple a biopsy cap to the biopsy port. The biopsy cap may have one more seals or sealing members. The seals may be designed to seal against the biopsy port and/or against instrument(s) that may be extended through the biopsy cap into the working channel. During some interventions, it may be desirable to secure the position of a medical instrument (e.g., a guidewire) relative to the endoscope. In order to secure the medical instrument, a locking mechanism may be secured to the endoscope and/or the biopsy cap. Disclosed herein are endoscope attachments or biopsy cap assemblies that may include a number of features including a biopsy cap housing, biopsy cap, a locking mechanism, as well as other features.

FIG. 1 illustrates a portion of a biopsy port 10 of an example endoscope 12. The biopsy port 10 may include a stem or neck region 14 and an end or flanged region 16. The biopsy port 10 serves as an access point to a channel (e.g., a working channel) of the endoscope 12. The biopsy port 10, in general, may be designed to receive a biopsy cap.

Figure 2:
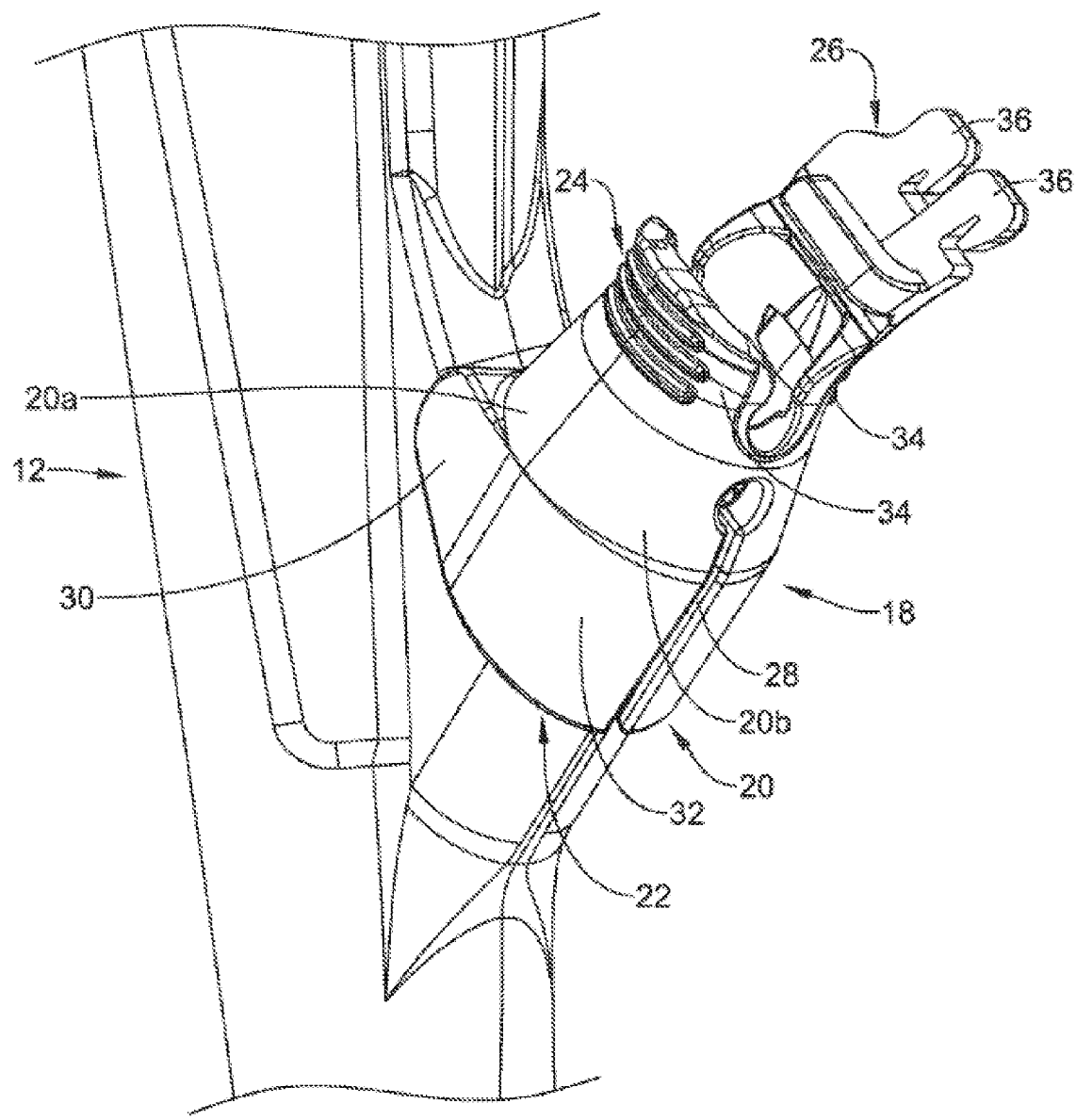
FIG. 2 is a plan view of an biopsy cap housing coupled to an endoscope, in accordance with an embodiment of the present disclosure.
Figure 3:
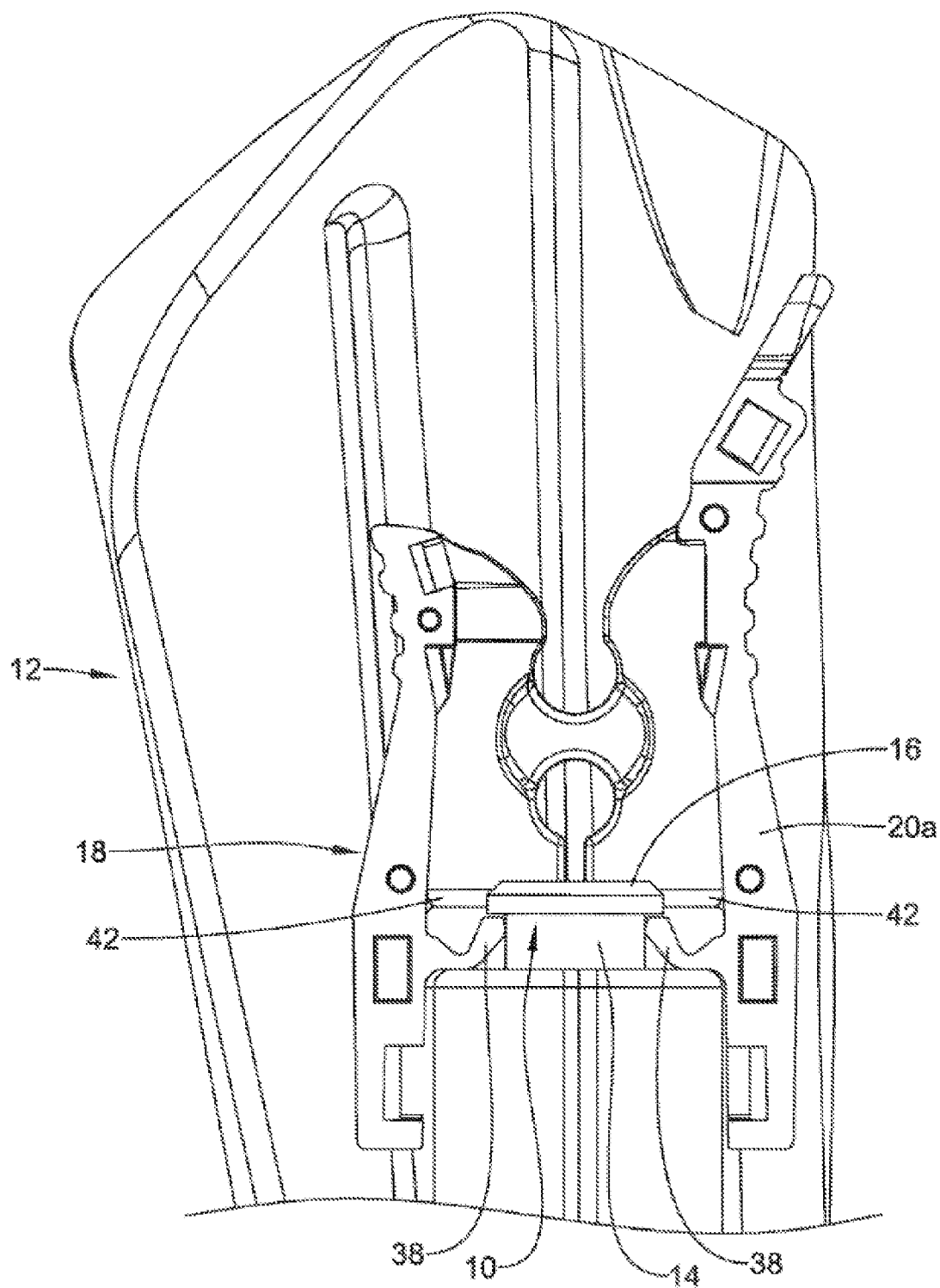
FIG. 3 is a side view of a portion of biopsy cap housing coupled to an endoscope, according to an embodiment of the present disclosure.

FIGS. 2-3 illustrates an example endoscope attachment 18 including a housing 20 coupled to the biopsy port 10. In general, the endoscope attachment 18 is designed to be coupled to (e.g., detachably coupled, attached, secured to, etc.) the biopsy port of an endoscope (e.g., the biopsy port 10 of the endoscope 12). In addition, the endoscope attachment 18 includes a number of features including the ability to form a seal with a biopsy cap at the biopsy port 10, allow for a medical instrument (e.g., a guidewire, catheter, endoscopic device, and/or the like) to pass therethrough and into the working channel of the endoscope 12, allow for the medical instrument to be secured relative to the endoscope 12, etc., and may be configured to securely receive a biopsy cap 300 (e.g. in FIG. 13 discussed herein).

The endoscope attachment 18 may include a housing 20 having a skirt region 22, a grip region 24, and a locking region 26. In some instances, the housing 20 may be a single piece. In other instances, the housing 20 may be formed from 2 or more pieces, for example, first housing portion 20a and second housing portion 20b, which are secured together. In FIG. 3, for example, the second housing portion 20b is removed and only the first housing portion 20a is shown. Forming the housing 20 from separate pieces may allow for the housing 20 to be relatively easily molded (e.g., compared to a singular piece) or otherwise formed into a complex shape. When formed from separate pieces, the housing portions 20a, 20b may be secured together in a suitable manner such as by pinning (e.g., snap locks that include pins on one portion and holes or openings to receive the pins on the other portion), thermal bonding, adhesive bonding, and/or the like. In various embodiments, the housing 20 may be substantially rigid. Pinning may result in secure attachment of the portions 20a, 20b and also may enhance the ability of the two portions 20a, 20b of the housing to "pivot" relative to one another. When doing so, the housing 20 can open or widen (e.g., adjacent to a lower portion of the endoscope attachment 18 such as adjacent to the skirt region 22) in order to attached/detach the endoscope attachment 18 to the biopsy port 10. A slot or opening 28 may be formed along a portion of the housing 20. The slot(s) may enhance the flexibility and/or pivoting ability of the housing 20 and may make it easier to secure the endoscope attachment 18 to the biopsy port 10.

The skirt region 22 may generally be designed to follow the shape and/or contour of the endoscope 12. More particularly, the skirt region 22 may be shaped so as to conform to the shape of the handle region of the endoscope 12 adjacent to the biopsy port 10. This may increase the stability of the endoscope attachment 18 and assist with securing hold of the position of the endoscope attachment 18 relative to the endoscope 12. In at least some instances, the shape of the skirt region 22 may be described as being asymmetrical. For example, the skirt region 22 may include a first portion 30 (e.g., which may or may not correspond to the first housing portion 20a) and a second portion 32 (e.g., which may or may not correspond to the second housing portion 20b).

The grip region 24 may include one or more gripping members 34. The gripping members 34 may take the form of finger or pinch grips that allow a user to grasp the endoscope attachment 18. In some instances, pinching together the gripping members 34 may widen the endoscope attachment 18 (e.g., adjacent to the skirt region 22) and allow for the endoscope attachment 18 to be more attached to/detached from the biopsy port 10. The slot 28 may help to facilitate the flexing/bending of the endoscope attachment 18 when the gripping members 34 are pinched.

The locking region 26 may include one or more locking apparatuses 36. The locking apparatuses 36 may vary in form. In some instances, the locking apparatuses 36 may take the form of hooks designed to engage and hold a medical instrument (e.g., a guidewire, catheter, endoscopic device, and/or the like). When doing so, the medical instrument can be held in place relative to the endoscope attachment 18 (and/or the endoscope 12).

Figure 4:
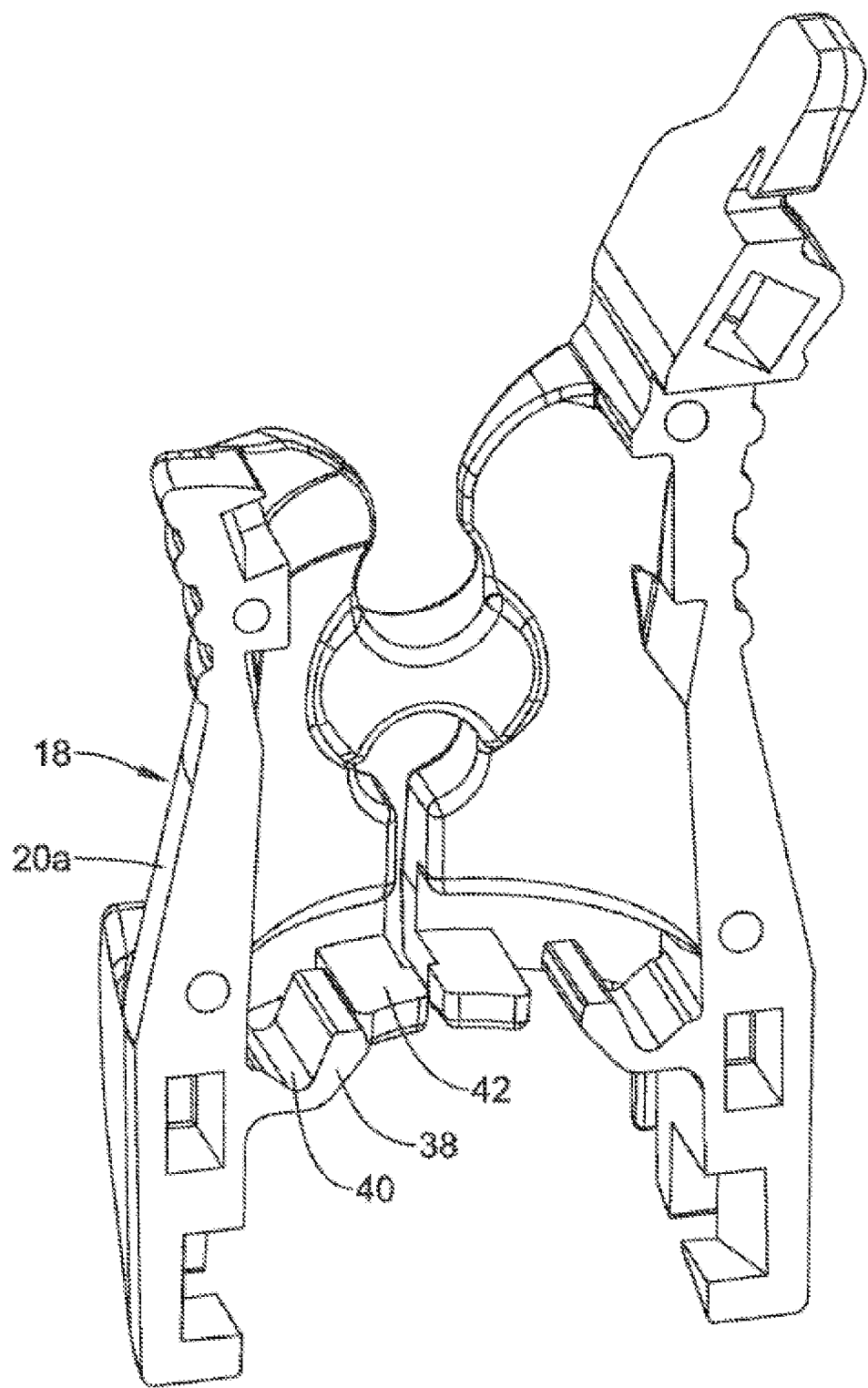
FIG. 4 is a perspective view of a portion of a biopsy cap housing, in accordance with an embodiment of the present disclosure.

As shown in FIGS. 3 and 4, housing 20 of the endoscope attachment 18 may include one or more angled locking members 38. In general, the angled locking members 38 take the form of projections that extend radially inward and in a direction toward an upper chamber from the inner surface of the housing 20. The angled locking members 38 may include a bend, jogged, or bent region 40. In at least some instances, the angled locking members 38 may be described as being "V-shaped". However, other shapes are contemplated. The angled locking members 38 may be resiliently flexible such that the angled locking members 38 can bend or deflect in order to fit over and secure to the flanged region 16 of the biopsy port 10. The number of angled locking members 38 and/or the arrangement of the angled locking members 38 may vary. For example, the housing 20 may include two, three, four, five, six, seven, eight, or more angled locking members 38. In some instances, each center-split halves 20a, 20b includes a pair of angled locking members 38 that are arranged across from or opposite one another. When the housing portions d20a, 20b are brought together, one of the angled locking members 38 from each of the opposing housing portions 20a, 20b may be disposed adjacent to one another. Other arrangements are contemplated.

The housing 20 of the endoscope attachment 18 may include one or more stabilizing members 42. In general, the stabilizing members 42 may take the form of take the form of projections that extend radially inward from the inner surface of the housing 20. The stabilizing members 42 may help to stabilize the position (e.g., laterally and/or axially) on the biopsy port 10. The number of stabilizing members 42 and/or the arrangement of the stabilizing members 42 may vary. For example, the housing may include two, three, four, five, six, seven, eight, or more stabilizing members 42. In some instances, each housing portion 20a, 20b includes a pair of stabilizing members 42 that are disposed adjacent to one another. When the housing portions 20a, 20b are brought together, the pairs of stabilizing members 42 from each of the opposing housing portions 20a, 20b may be disposed opposite to one another. Other arrangements are contemplated.

Figure 5A:
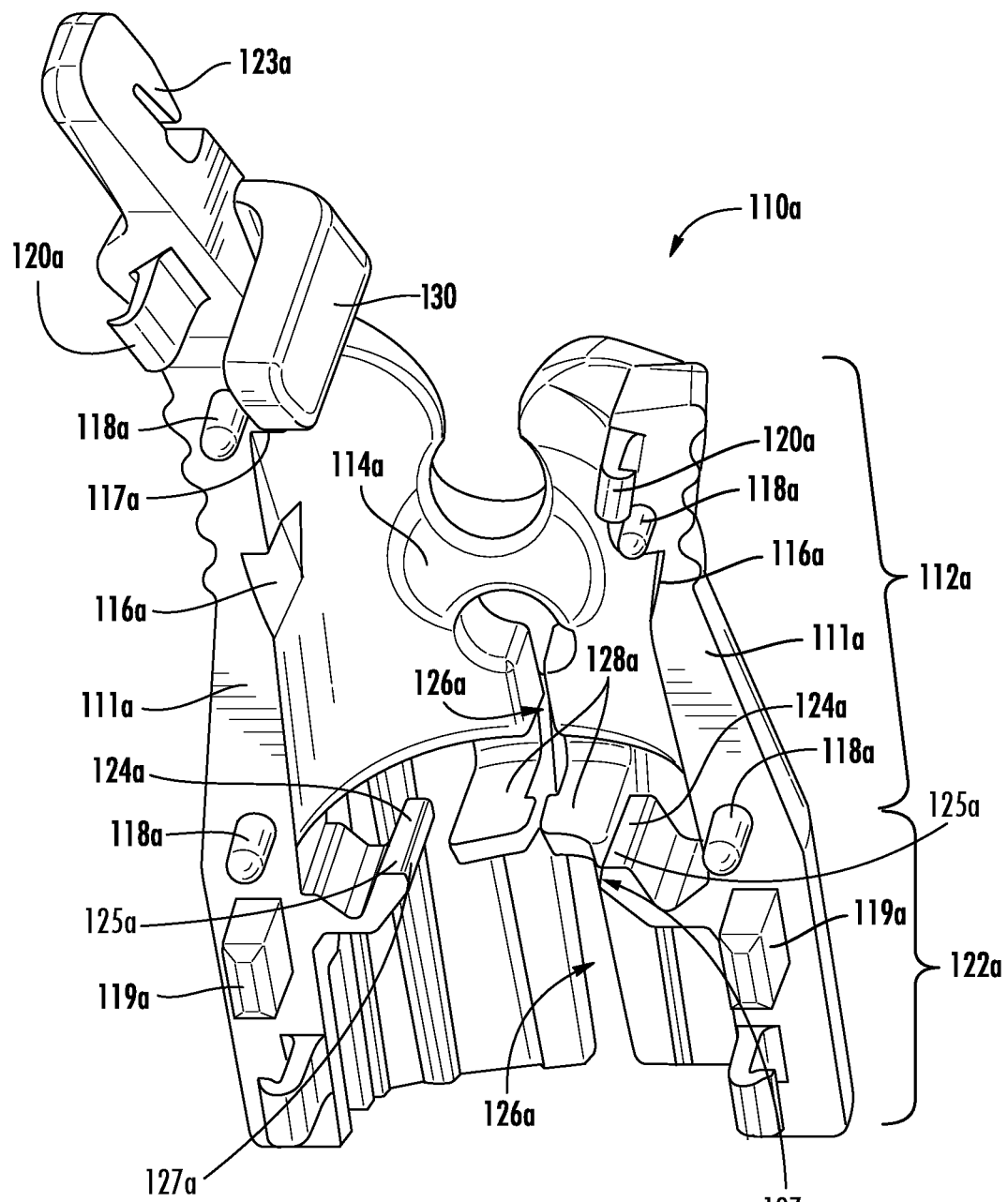
FIGS. 5A-5C provide perspective views of center-split halves of a biopsy cap housing, according to an embodiment of the present disclosure.
Figure 5C:
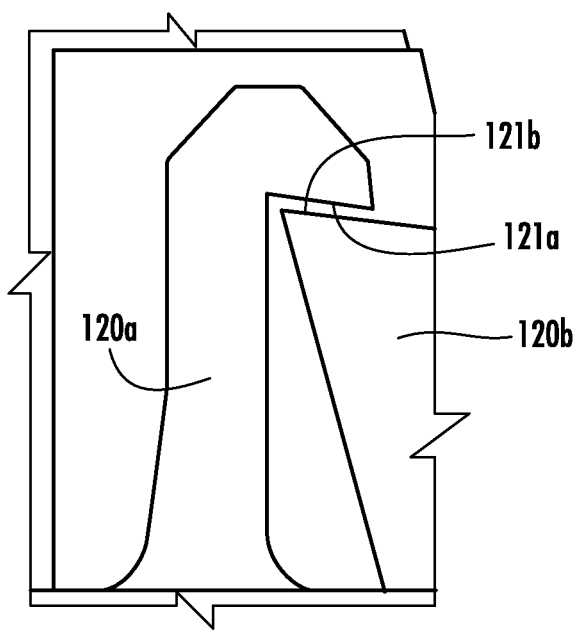
Figure 5B:
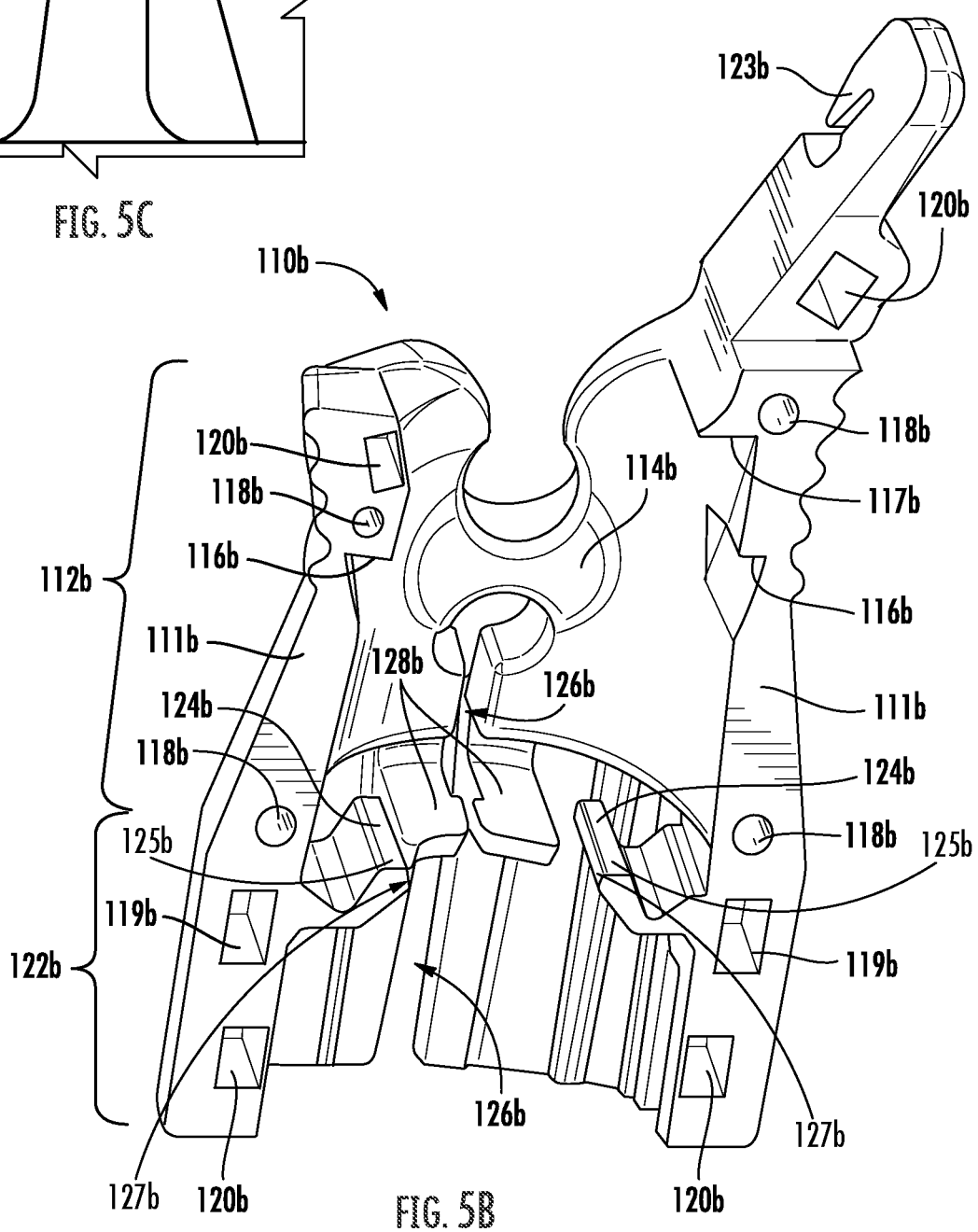
Figure 6A:
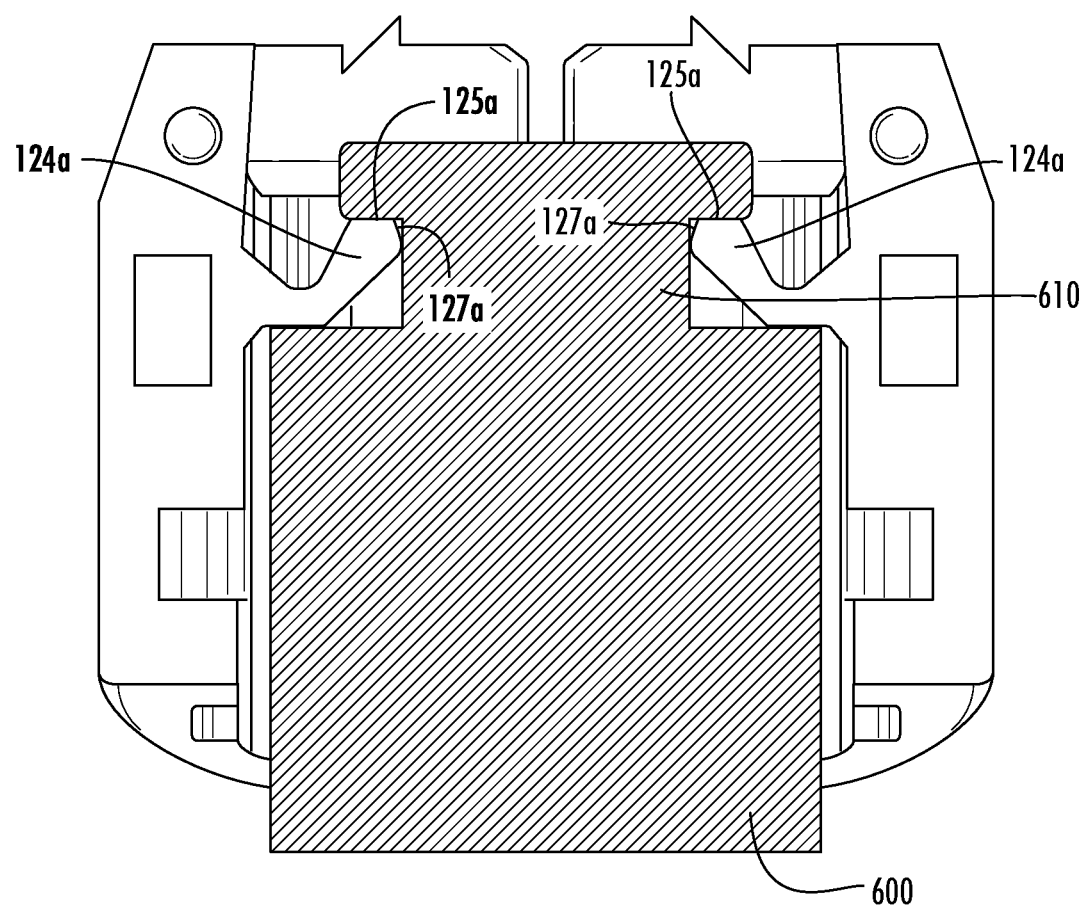
FIGS. 6A-6C are perspective views of a biopsy cap housing, according to an embodiment of the present disclosure.

Referring to FIGS. 5A and 5B, an embodiment of a biopsy cap housing of the present disclosure may include first and second center-split halves 110a, 110b (e.g., first and second housing portions or pieces) configured to mate or interlock with each other to define a first portion 112a, 112b, (e.g., an upper chamber, first chamber, top chamber, etc.) configured to securely receive a biopsy cap 300 (e.g. in FIG. 13 discussed herein) and a second portion 122a, 122b, (e.g., a lower chamber, second chamber, bottom chamber, etc.) configured to securely and reversibly engage the neck 610 of an endoscope biopsy port 600 (e.g. in FIG. 6A discussed herein).

Referring to FIG. 5A, in an embodiment, a first center-split half 110a (e.g., first side, lock side, etc.) of the biopsy cap housing (e.g., such as the housing 20 of FIGS. 2-4) may include a first (e.g., top, upper) portion 112a defining a first half (e.g., a substantially hemi-cylindrical half) of the upper chamber, and a second (e.g., bottom, lower) portion 122a defining a first half (e.g., a substantially hemi-cylindrical half) of the lower chamber. A first locking hook 123a (e.g., guidewire locking hook) and a guide 130 may be attached to or integrally formed with a proximal end of the first portion 112a. A first pivot member 114a (e.g., first pivot button, first pivot feature, etc.) may be integrally formed with an approximate midpoint of the first portion 112a, and a first slit 126a (e.g., opening, slot, etc.) may extend through a sidewall of the first and second portions 112a, 122a and in substantial alignment with (e.g., on the same side as, directly below, etc.) the first pivot member 114a. The first pivot member 114a may include a substantially radially raised or elevated surface (e.g., enlarged portion, projection, etc.) extending into the first half of the upper chamber, e.g., to engage a corresponding recessed portion 312a formed within an outer wall of a biopsy cap 300 (e.g. in FIG. 13 discussed herein).

In an embodiment, an inner surface of the first portion 112a of the first center-split half 110a may include a surface feature(s) configured to compressingly and/or frictionally engage a corresponding surface feature of a biopsy cap. In some embodiments, the surface feature(s) may include a lip 117a (e.g., step feature, etc.) integrally formed with an inner wall of the first center-split half 110a and extending into the first half of the upper chamber at or near a proximal end of the first portion 112a. In various embodiments, the surface feature(s) may include a pair of wedges 116a (e.g., indentations, recessed portions, etc.) formed within the inner wall of the first portion 112a distal to the lip 117a and on opposite sides (e.g., separated by approximately 180 degrees) of the first half of the first portion 112a.

In an embodiment, one or more locking members 124a (e.g., V-locks, etc.) may be attached to or integrally formed with an inner wall of the first center-split half 110a at or near a proximal end of the second portion 122a and on opposite sides (e.g., separated by approximately 180 degrees) of the first half of the second portion 122a. The locking member(s) 124a may be configured to releasably engage a biopsy port 600 (e.g., at the neck 610) disposed within the second portion 122a (e.g. in FIG. 6A discussed herein). For example, an end of the locking member(s) 124a may include a pair of substantially perpendicular surfaces 125a, 127a configured to engage (e.g., contact, fit within, e.) a substantially 90-degree surface (e.g., a bottom or lower surface of a lip) of the neck 610 of the biopsy port 600 or alternatively with stabilizing members 128a if radially deformed without a biopsy port 600 (as will be discussed with reference to FIGS. 6A-6C below). In addition, one or more platforms (e.g., stops, etc.) may be attached to or integrally formed with an inner wall of the first center-split half 110a on opposite sides of the first slit 126a and between the locking member(s) 124a.

In an embodiment, one or more projections may be attached to or integrally formed with a mating surface 111a of the first and second portions 112a, 122a of the first center-split half 110a. In various embodiments, the projection(s) may include one or more pins 118a (e.g., posts, rods, etc.) with a substantially spherical or cylindrical outer dimension. In various additional embodiments, the projections(s) may include one or more pegs 119a (e.g., blocks, etc.) with a substantially square or rectangular outer dimension. In various additional embodiments, the projections(s) may include one or more snap-locks 120a (e.g., arms, etc.) with a substantially curved or hooked end.

By way of non-limiting example, in an embodiment, two pins 118a may extend from the mating surface 111a at or near a proximal end of the first portion 112a and two pins 118a may extend from the mating surface 111a adjacent to the locking member(s) 124a. Two snap-locks 120a may extend from the mating surface 111a at or near the proximal end of the first portion 112a and proximal to the pins 118a and two snap-locks may extend from the mating surface 111a at or near a distal end of the second portion 122a. Two pegs 119a may extend from the mating surface 111a adjacent to the locking member(s) 124a, distal to the pins 118a and proximal to the pegs 119a.

Referring to FIG. 5B, in an embodiment, a second center-split half 110b (e.g., second side, groove side, etc.) of the biopsy cap housing (e.g., such as the housing 20 of FIGS. 2-4) may include a first (e.g., top) portion 112b defining a second half (e.g., a substantially hemi-cylindrical half) of the upper chamber, and a second (e.g., bottom) portion 122b defining a second half (e.g., a substantially hemi-cylindrical half) of the lower chamber. A second locking hook 123b (e.g., guidewire locking hook) may be attached to or integrally formed with a proximal end of the first portion 112b. A second pivot member 114b (e.g., second pivot button, second pivot feature, etc.) may be integrally formed with an approximate midpoint of the first portion 112b, and a second slit 126b (e.g., opening, slot, etc.) may extend through a sidewall of the first and second portions 112b, 122b and in substantial alignment with (e.g., one the same side as, directly below, etc.) the second pivot member 114b. The second pivot member 114b may include a raised or elevated surface (e.g., enlarged portion, etc.) extending into the first half of the upper chamber, e.g., to engage a corresponding recessed portion 312b (e.g., groove, indentation, etc.) formed within an outer wall of a biopsy cap 300 (e.g. in FIG. 13 discussed herein).

In an embodiment, an inner surface of the first portion 112b of the second center-split half 110b may include a surface feature(s) configured to compressingly and/or frictionally engage a corresponding surface feature of a biopsy cap. In an embodiment, the surface feature(s) may include a lip 117b (e.g., step feature, etc.) integrally formed with an inner wall of the second center-split half 110b and extending into the first half of the upper chamber at or near a proximal end of the first portion 112b. In an embodiment, the surface feature(s) may include a pair of wedges 116b (e.g., indentation, recessed portion, etc.) formed within the inner wall of the second portion 112b distal to the lip 117b and on opposite sides (e.g., separated by approximately 180 degrees) of the first half of the first portion 112b.

In an embodiment, one or more locking members 124b (e.g., V-locks, etc.) may be attached to or integrally formed with an inner wall of the second center-split half 110b at or near a proximal end of the second portion 122b and on opposite sides (e.g., separated by approximately 180 degrees) of the second half of the lower chamber. The locking member(s) 124b may be configured to releasably engage the neck 610 of a biopsy port 600 disposed within the lower chamber (FIG. 6A). For example, an end of the locking member(s) 124b may include a pair of substantially perpendicular surfaces 125b, 127b configured to engage (e.g., contact, fit within, etc.) a substantially 90-degree surface (e.g., a bottom or lower surface of a lip) of the neck 610 of the biopsy port 600 or alternatively with stabilizing members 128b if radially deformed without a biopsy port 600 (as will be discussed with reference to FIGS. 6A-6C below). In addition, one or more platforms 128b (e.g., stops, etc.) may be attached to or integrally formed with an inner wall of the second center-split half 110b on opposite sides of the second slit 126b and between the locking member(s) 124b.

In an embodiment, one or more receiving elements (e.g., receiving features, etc.) may be integrally formed within a mating surface 111b of the first and second portions 112b, 122b of the second center-split half 110b and configured to receive/engage the corresponding one or more projection(s) of the first center-split half 110a in a friction or interference fit, e.g., such that the first and second center-split halves 110a, 110b may interlock in a snap-fit configuration to form an assembled biopsy cap housing. In various embodiments, the receiving element(s) may include one or more pin holes 118b (e.g., posts, rods, etc.) with a substantially spherical or cylindrical inner dimension configured to frictionally receive the corresponding substantially spherical or cylindrical outer dimension of the respective pin(s) 118a. In various additional embodiments, the receiving element(s) may include one or more sockets 119b with a substantially square or rectangular inner dimension configured to frictionally receive the corresponding substantially square or rectangular outer dimension of the respective peg(s) 119a. In various additional embodiments, the receiving element(s) may include one or more snap-lock receivers 120b with a substantially curved or hooked inner dimension configured to receive the corresponding substantially curved or hooked end of the snap-lock(s) 120a. Referring to FIG. 5C, in an embodiment, the one or more snap-locks 120a of the present disclosure may include a recessed angled surface 121a configured to frictionally and/or compressingly contact/engage a corresponding angled surface 121b of the respective or more snap-lock receivers 120b. In various embodiments, the interface between these opposing angled surfaces may provide a "positive locking" interaction with a greater locking force/interaction than between corresponding non-angled surfaces.

By way of non-limiting example, in an embodiment, two pin holes 118b may be formed within the mating surface 111b at or near a proximal end of the first portion 112b and two pin holes 118b may be formed within the mating surface 111b adjacent to the locking member(s) 124b. Two snap-lock receivers 120b may be formed within the mating surface 111b at or near the proximal end of the first portion 112b and proximal to the pin holes 118b and two snap-lock receiver 120bs may be formed within the mating surface 111b at or near a distal end of the second portion 122b. Two sockets 119b may be formed within the mating surface 111b adjacent to the locking member(s) 124b, distal to the pin holes 118b and proximal to the snap-lock receivers 120b.

In an embodiment, a biopsy cap housing of the present disclosure may be assembled by aligning the mating surfaces 111a, 111b of the first and second center-split halves 110a, 110b such that each of the one or more projections (e.g., pin(s) 118a, peg(s) 119a and snap-lock(s) 120a) is aligned with the corresponding one or more receiving elements (e.g., pin hole(s) 118b, socket(s) 119b and snap-lock receiver(s) 120b) and then compressing or squeezing the first and second center-split halves 110a, 110b together in a snap-fit configuration. In various embodiments, the first and second locking hooks 123a, 123b may be substantially adjacent to each other when the biopsy cap housing is assembled and configured to securely engage a proximal portion of a guidewire. In addition, the respective surface features of the first portions 112a, 112b of the first and second center-split halves 110a, 110b may be substantially aligned to provide contiguous surface features to prevent or limit axial and/or rotational movement of a biopsy cap 300 (e.g. in FIG. 13 discussed herein) disposed within the upper chamber and/or to prevent fluid flow (e.g., leakage) around an outer surface of the biopsy cap 300. For example, the lips 117a, 117b of the first and second portions 112a, 112b may align to form a substantially contiguous lip extending into the upper chamber at or near a proximal end of the biopsy cap housing and the wedges 116a, 116b may substantially align to form contiguous wedges on opposites sides of the upper chamber.

Figure 6B:
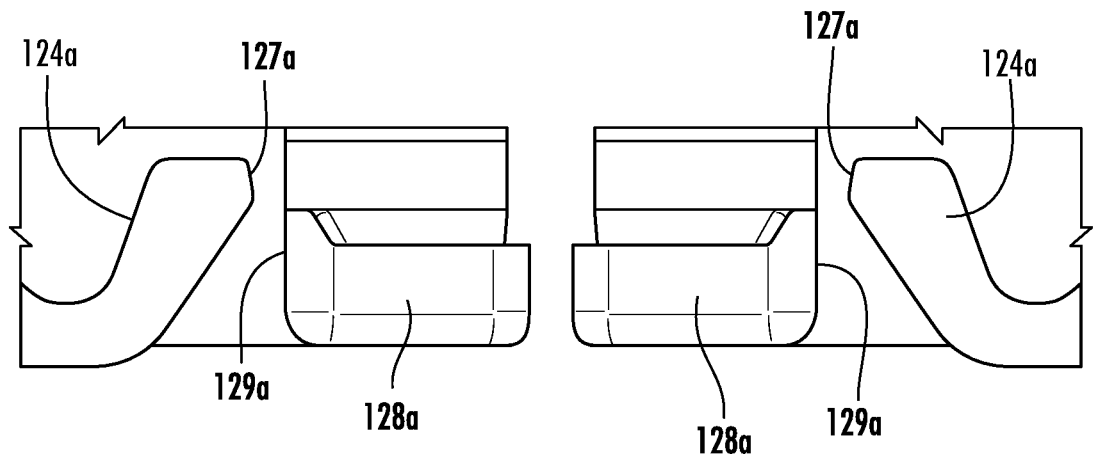
Figure 6C:
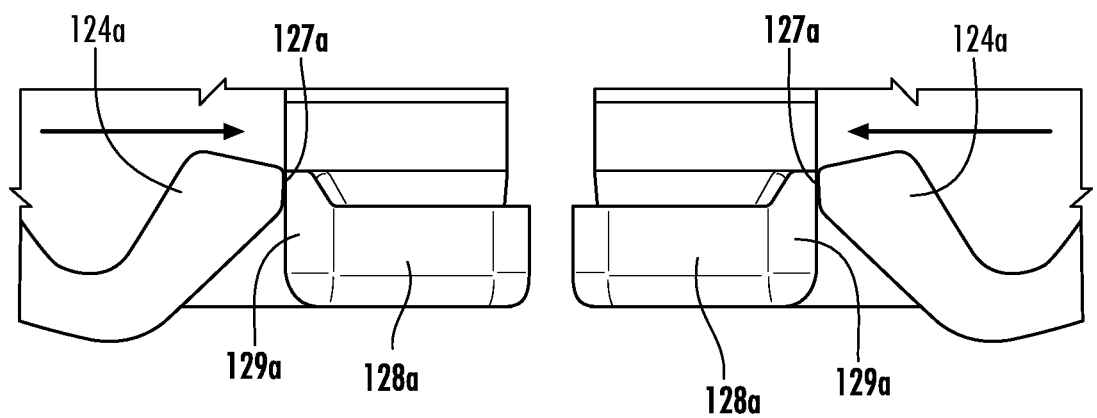

Referring to FIG. 6A, in an embodiment, the locking members 124a (e.g., V-locks, etc.) may releasably engage the neck 610 of a biopsy port 600 disposed within the lower chamber, e.g., when the second portions (e.g. second portions 122a, 122b of FIGS. 5A and 5B) of the biopsy cap housing (e.g., such as the housing 20 of FIGS. 2-4) are inwardly compressed towards each other. The locking members 124a may be the locking members 38 of FIGS. 3 and 4, the locking members 124a, 124b of FIGS. 5A and 5B, or may be of another embodiment of a housing. Referring to FIG. 6B, in a resting state and without a biopsy port 600, the locking members 124a may be separated by a distance from a surface 129a (e.g., enlarged or thickened surface) of a respective platform of the substantially perpendicular stabilizing members 128a. Referring to FIG. 6C, with the locking members radially urged toward each other without a biopsy port 600 (e.g., when the first portions 112a, 112b of the biopsy cap housing are inwardly compressed towards each other), the ends of the locking members 124a may contact the respective surface 129a of the stabilizing members 128a, thereby preventing the locking members 124a from overextending to a point of fracture. For example, the surfaces 129a may prevent the locking members 124a from extending past the respective the platforms 128a to a point at which one or both of the locking members 124a may break or otherwise fracture (e.g., the surfaces 129a may be substantially perpendicular to the radial flexure of the first locking member or second locking member). By way of non-limiting example, the platform 128a may be configured or positioned to allow the locking members 124a to bend or flex a number of degrees (e.g., approximately 15-degrees and not greater than approximately 25-degrees.

As will be understood by those of skill in the art, the substantially equal distribution of forces throughout the biopsy cap housing, including radially outward forces due to device exchange or guidewire locking and high-stress forces at the pivot points due to attachment/removal from the biopsy port, may reduce the cumulative effects of wear-and-tear resulting from incremental and persistent movement between the interlocking projections and receiving elements and/or prevent partial or complete disengagement of the lower housing from the neck 610 of the endoscope biopsy port 600.

Figure 7:
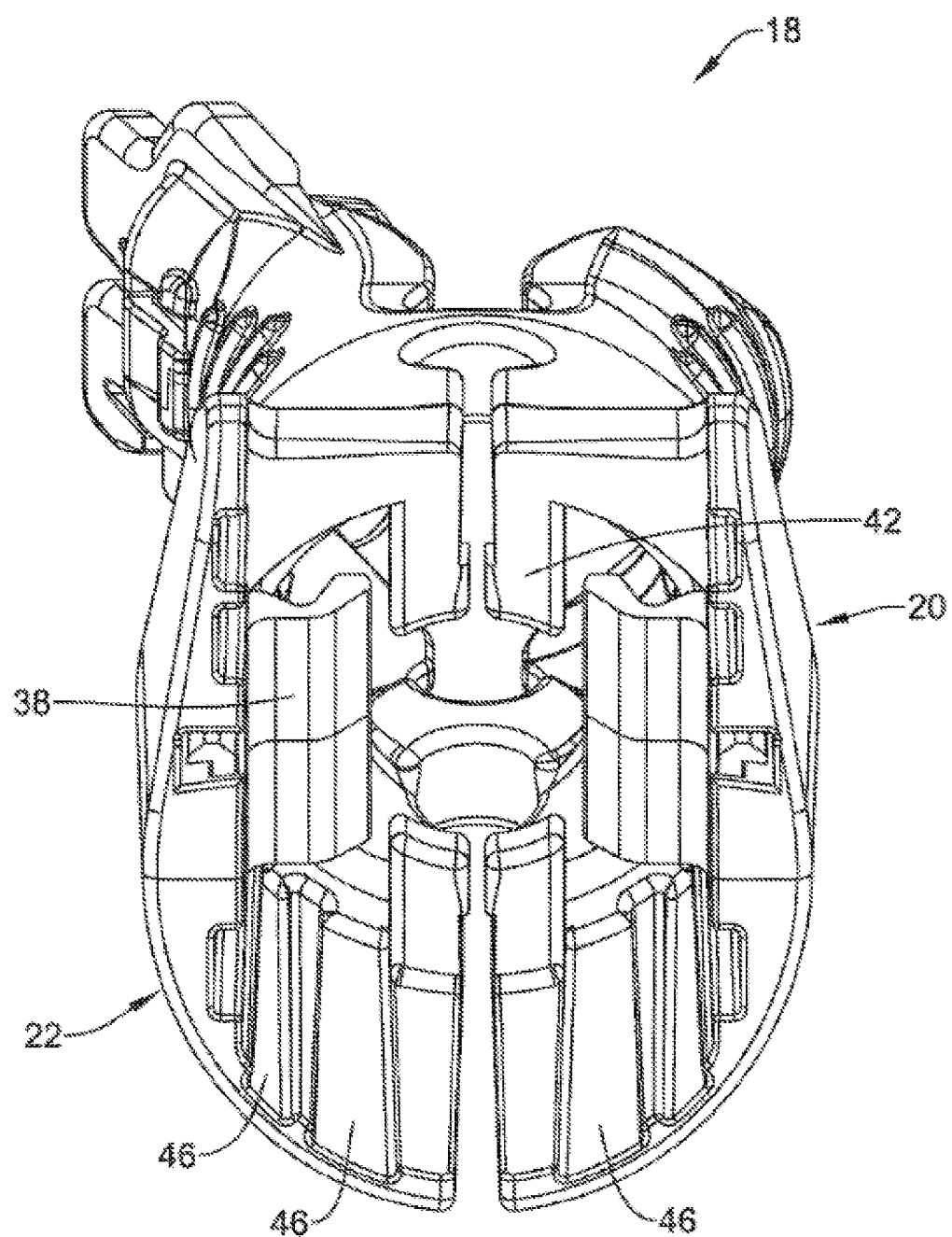
FIG. 7 is a perspective view of a biopsy cap housing, according to an embodiment of the present disclosure.

In an embodiment, a skirt region 22 may have one or more gripping members or ribs 46 disposed along an inner surface (e.g., an inner surface of the housing 20 at or along the skirt region 22) as shown in FIG. 7. The ribs 46 may help to form or otherwise define a surface along the interior of the endoscope attachment 18 that allows the endoscope attachment 18 to "grip" onto and/or otherwise frictionally engage the endoscope 12 and, thus, help to secure the endoscope attachment 18 to the endoscope 12.

Figure 8:
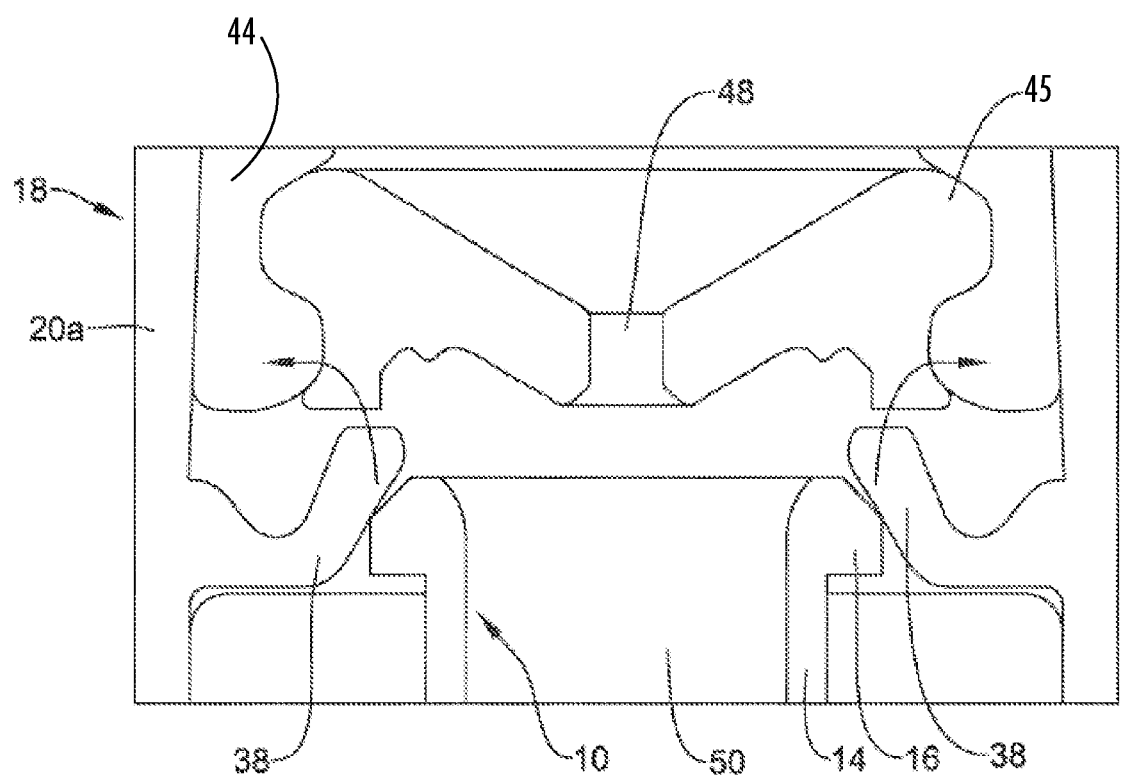
FIGS. 8 and 9 depict a biopsy cap housing being coupled to an endoscope, according to an embodiment of the present disclosure.
Figure 9:
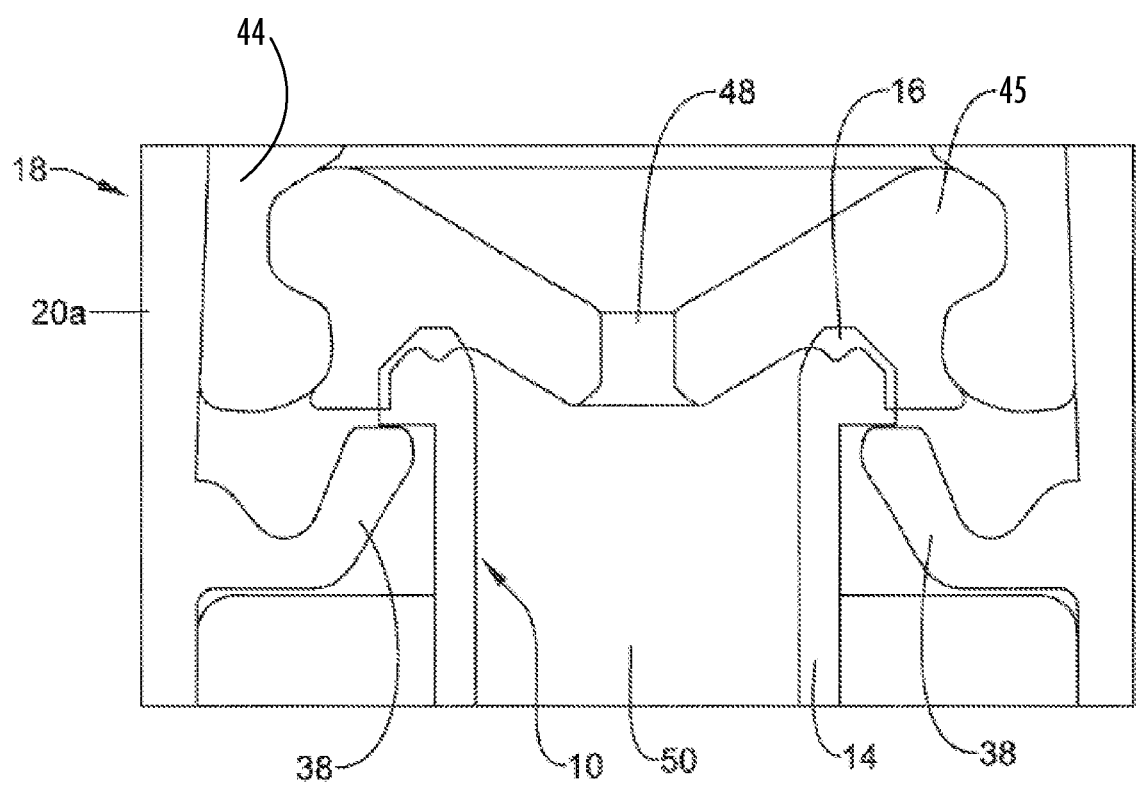

FIGS. 8 and 9 depict an embodiment of an endoscope attachment 18 with housing 20 being attached to a biopsy port 10. For example, the endoscope attachment 18 may be disposed adjacent to the biopsy port 10. When doing so, the angled locking members 38 may be brought adjacent to the flanged region 16 of the biopsy port as shown in FIG. 8. A user may apply a force (e.g., a pinching force) along a grip region (e.g., the grip region 24 of FIG. 2) of the attachment 18 to outwardly flex or otherwise pivot in order to open or widen the housing 20 (e.g., adjacent to the skirt region 22). The user may also apply a downward force onto the endoscope attachment 18 to bring the endoscope attachment into engagement with and secure the endoscope attachment 18 to the biopsy port 10. When doing so, the angled locking members 38 may resiliently deflect so that the angled locking members 38 are seated underneath the flanged region as shown in FIG. 9. When secured, the stabilizing members 42 may engage the neck region 14 and/or the flanged region 16 of the biopsy port 10. Securing the endoscope attachment 18 to the biopsy port 10 may also bring an aperture 48 of seal member or a base 45 into engagement with the biopsy port 10 so that the seal member 48 may press against or otherwise seal a channel 50 of the endoscope 12 (e.g., a channel 50 accessible via the biopsy port 10). When the endoscope attachment 18 is secured to the biopsy port 10, the endoscope attachment 18 may provide haptic feedback such as a "snap" or "click" sound and/or sensation, and/or the like. A user may remove the endoscope attachment 18 by simply pinching the grip region 24 in order to flex/pivot/widen the housing 20 (as well as widen/open the angled locking members 38) and pulling the endoscope attachment 18 from the biopsy port 10.

Figure 10:
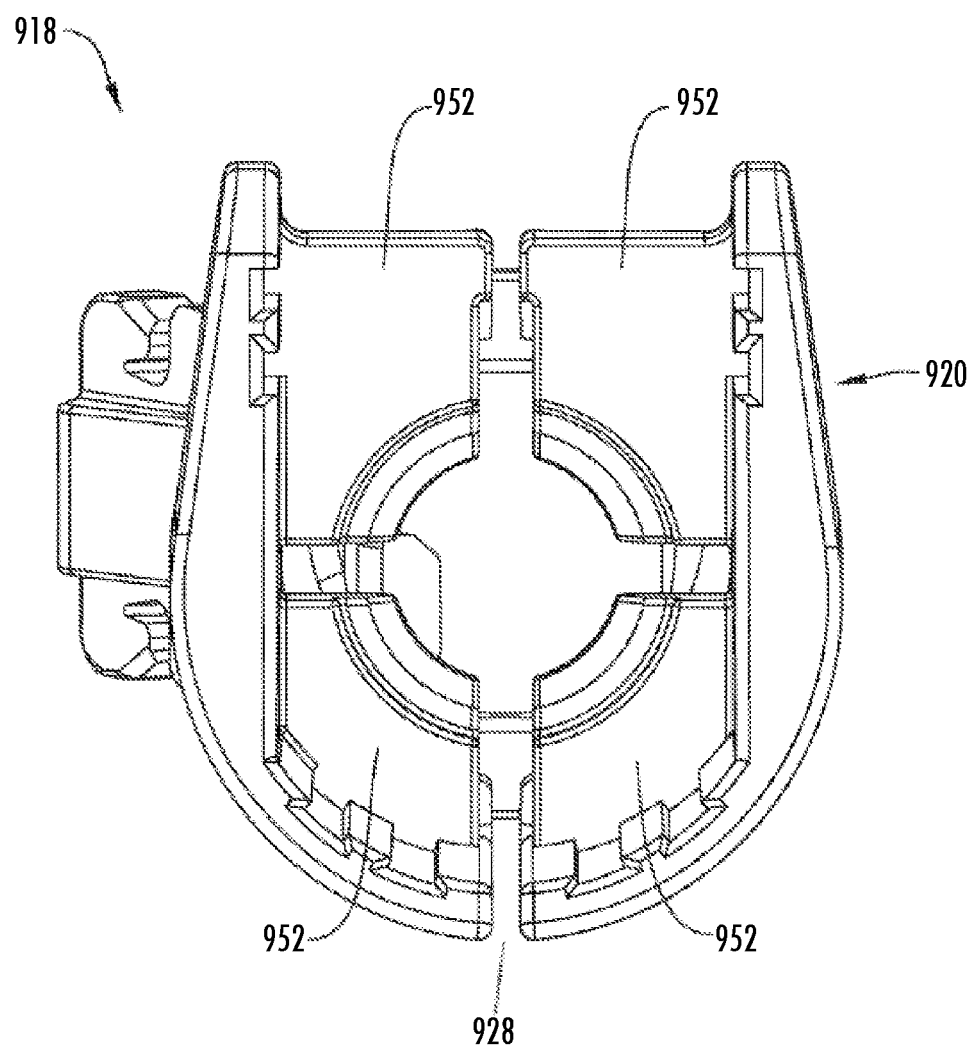
FIG. 10 is a perspective view of a biopsy cap housing, according to an embodiment of the present disclosure.

FIG. 10 illustrates an embodiment of an endoscope attachment 918 that may be similar in form and function to other endoscope attachments disclosed herein. The endoscope attachment 918 may include a housing 920. The housing 920 may be generally more flexible than the housing 20 in FIG. 2 or FIGS. 5A-5C. A slot 928 may be formed in the housing to further enhance the flexibility of the housing. One or more locking members 952 may extend from the housing 920. In some instances, the locking members 952 may take the form of substantially rigid projections that extend radially inward from the housing 920. In at least some instances, the locking members 952 may be arranged to form a generally circular (e.g., and/or a broken circle) lock designed to extend around a biopsy port (e.g., such as a biopsy port 10).

Figure 11:
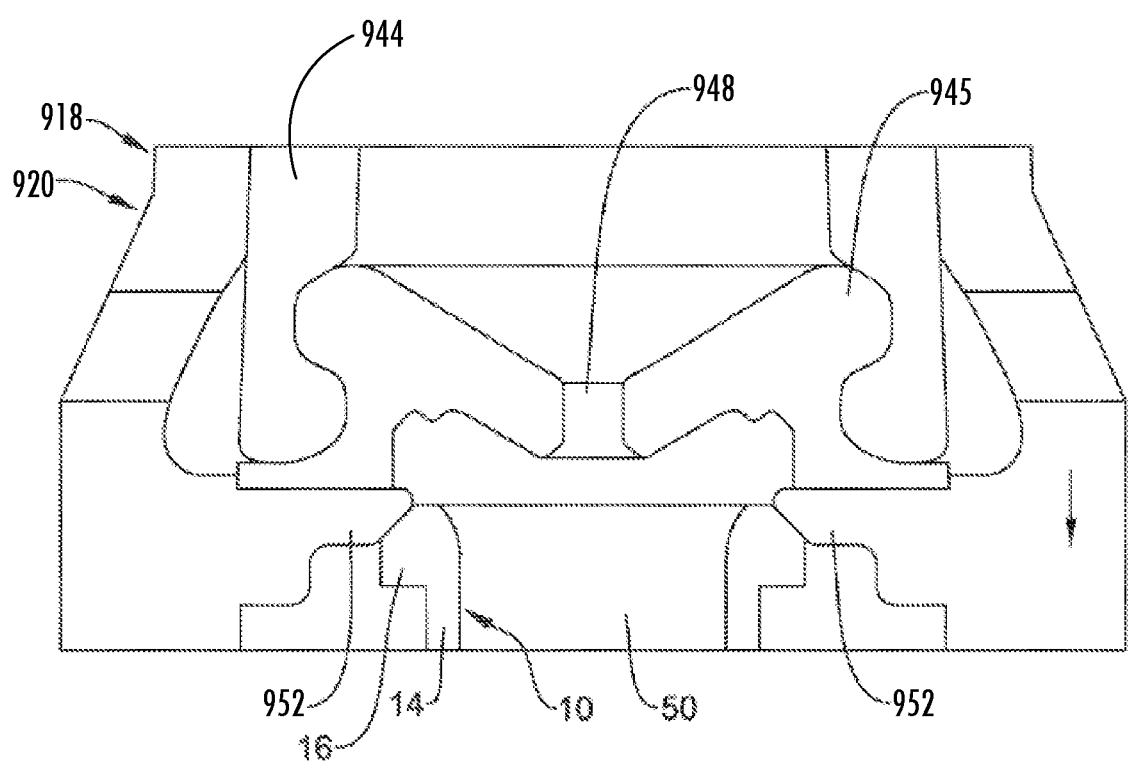
FIGS. 11 and 12 depict a biopsy cap housing being coupled to an endoscope.
Figure 12:
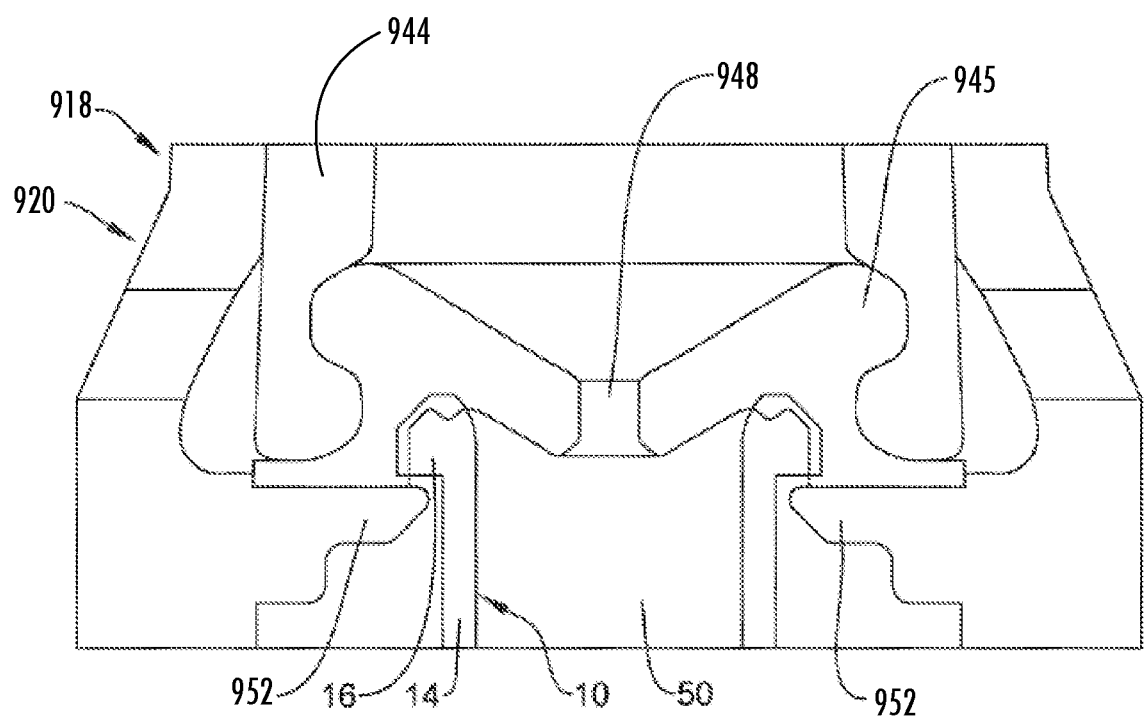

FIGS. 11 and 12 depict the endoscope attachment 918 of FIG. 10 being attached to a biopsy port 10. For example, the endoscope attachment 918 may be disposed adjacent to the biopsy port 10. When doing so, the locking members 952 may be brought adjacent to the flanged region 16 of the biopsy port as shown in FIG. 11. A user may apply a downward force onto the endoscope attachment 918 to secure the endoscope attachment 918 to the biopsy port 10. When doing so, the housing 920 may resiliently deflect so that the locking members 952 may be seated underneath the flanged region as shown in FIG. 12. Securing the endoscope attachment 918 to the biopsy port 10 may also bring an aperture 948 of seal member or a base 945 into engagement with the biopsy port 10 so that the base 945 may press against or otherwise seal a channel 50 of the endoscope 12 (e.g., a channel 50 accessible via the biopsy port 10). When the endoscope attachment 918 is secured to the biopsy port 10, the endoscope attachment 918 may provide haptic feedback such as a "snap" or "click" sound.

Figure 13:
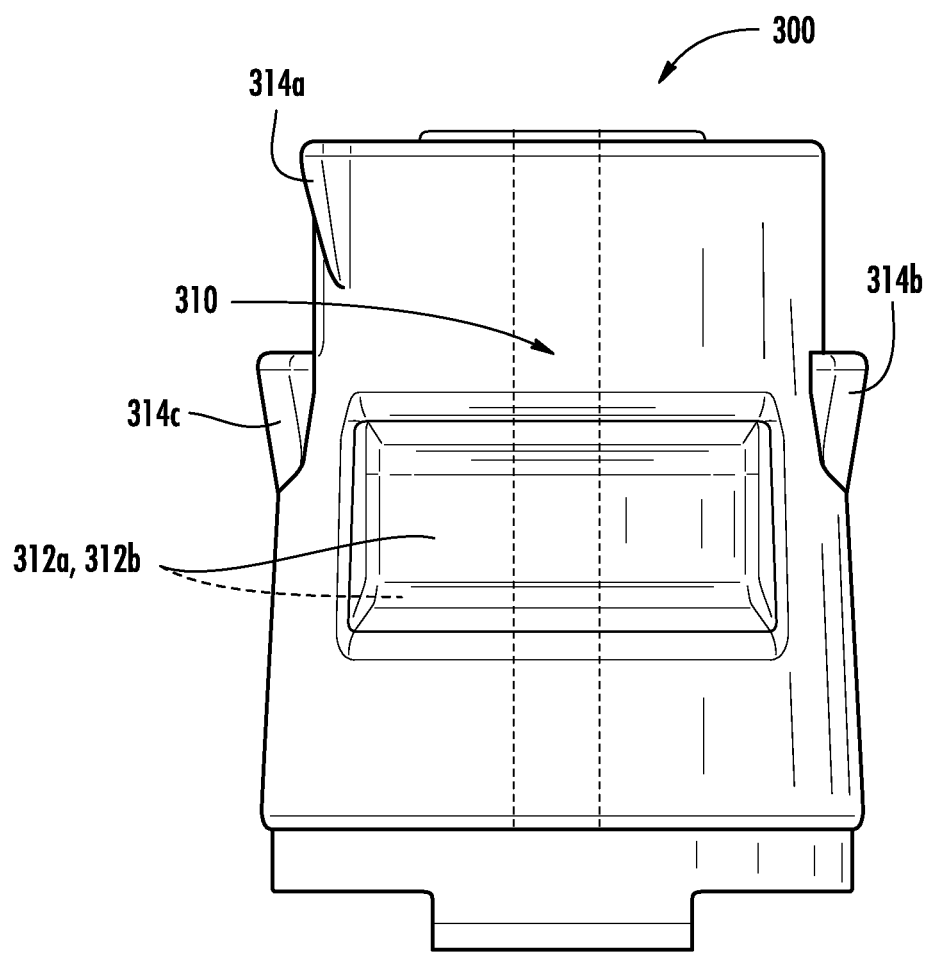
FIG. 13 is a perspective view of a biopsy cap, according to an embodiment of the present disclosure.

Referring to FIG. 13, in an embodiment, a biopsy cap 300 of the present disclosure may include a surface feature(s) formed on or within the biopsy cap 300 and configured to frictionally and/or compressingly engage a corresponding surface feature formed on or within an inner surface of the first portions of the first and second center-split halves (e.g. the first and second center-split halves 110a, 110b of FIGS. 5A and 5B). In an embodiment, the biopsy cap 300 may include a first surface feature 314a attached to or integrally formed with a proximal end (e.g., top surface) of the biopsy cap 300 and second and third surface features 314b, 314c attached to or integrally formed with an outer wall of the biopsy cap 300. In addition, or alternatively, the surface feature(s) may include first and second recessed portions 312a, 312b integrally formed within an outer wall of the biopsy cap 300 and separated from the second and third surface features 314b, 314c by approximately 90-degrees relative to an outer circumference of the biopsy cap 300. In various embodiments, a biopsy cap 300 of the present disclosure may be formed from or otherwise include a variety of compressible materials (e.g., silicone, rubbers, etc.) formed as a single unitary structure using, e.g., co-extrusion or co-molding techniques as are known in the art.

Figure 14:
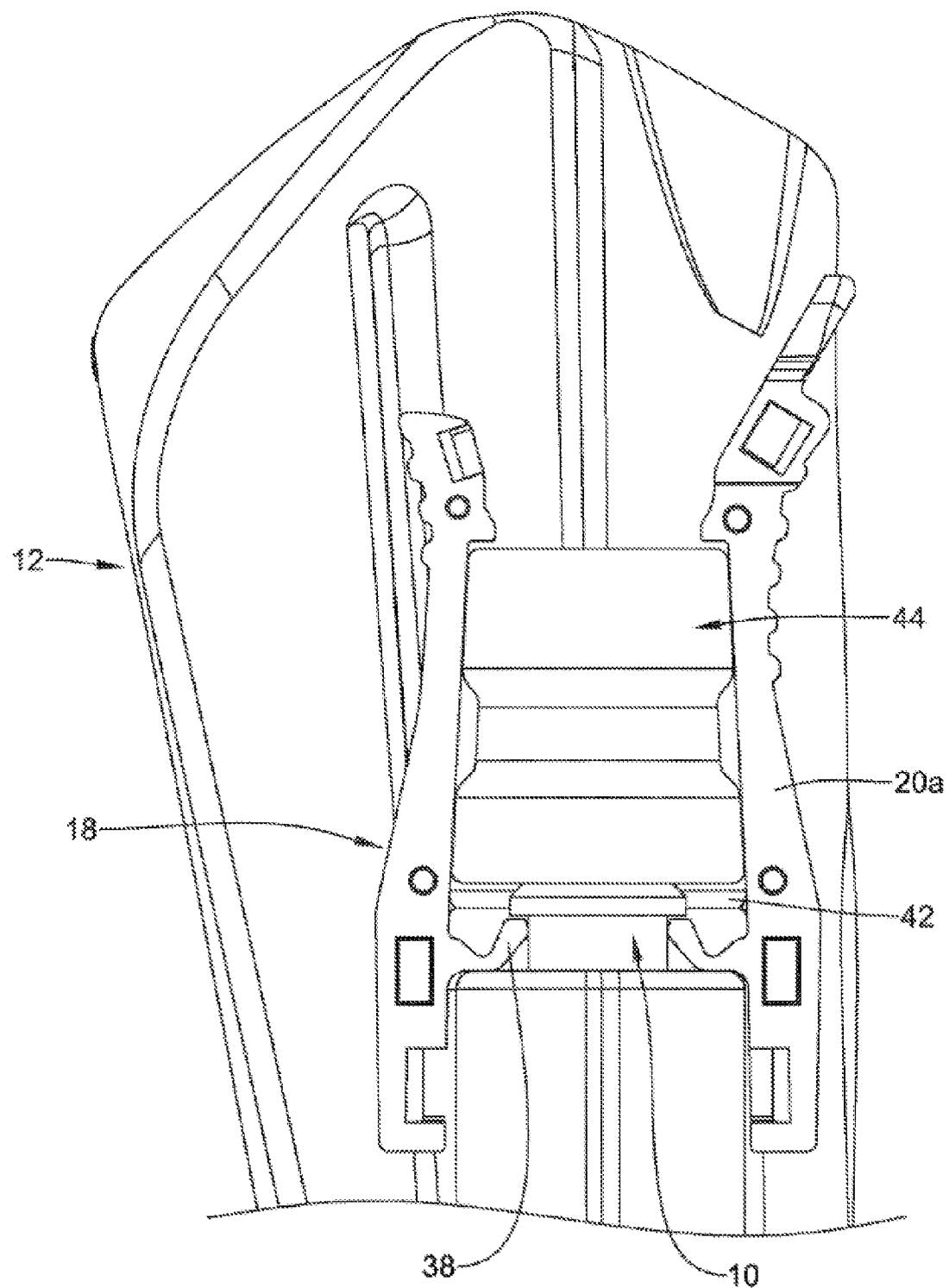
FIG. 14 is a side view of a portion of a biopsy cap housing coupled to an endoscope, according to an embodiment of the present disclosure.

With reference to FIG. 14, an embodiment of a biopsy cap 44 may be disposed within the housing 20 (e.g. of FIGS. 2. 5A-5C) of the endoscope attachment 18. It is noted that for clarity purposes, the biopsy cap 44 is not shown in FIGS. 2-5C. The biopsy cap 44 may vary in form. In at least some instances, the biopsy cap 44 may include one or more seals or sealing members (not depicted in FIG. 14). The seal(s) may be designed to seal against the biopsy port 10 and thereby prevent fluid from leaking from the biopsy port 10. In addition, the seal(s) may be designed to seal against a medical instrument (e.g., a guidewire, catheter, endoscopic device, and/or the like) passing through the biopsy cap 44 of endoscope attachment 18. In at least some instances, the biopsy cap 44 may be disposed adjacent to and/or otherwise seated on the stabilizing members 42.

Figure 15A:
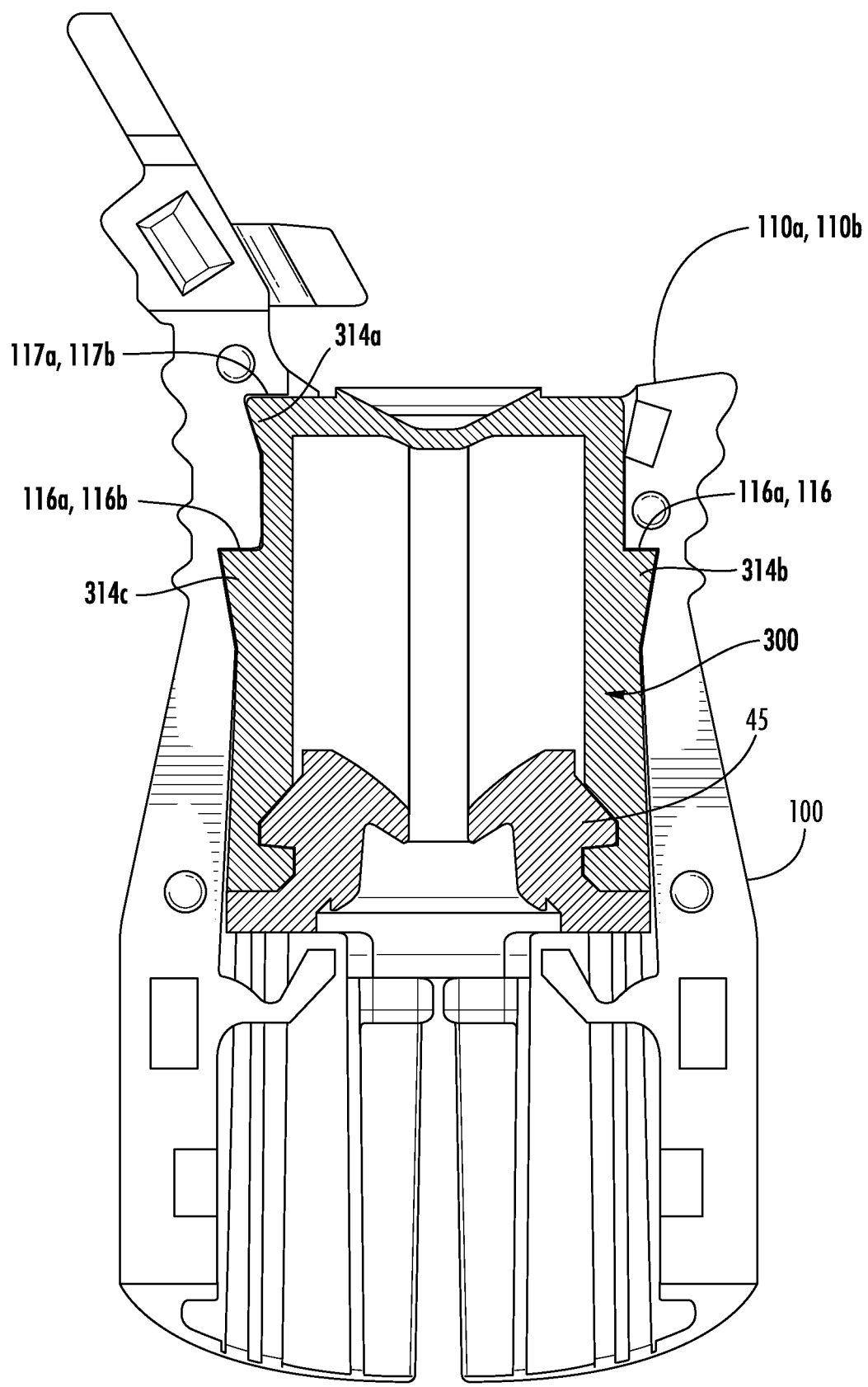
FIGS. 15A and 15B provide perspective views of a biopsy cap disposed within a biopsy cap housing, according to an embodiment of the present disclosure.
Figure 15B:
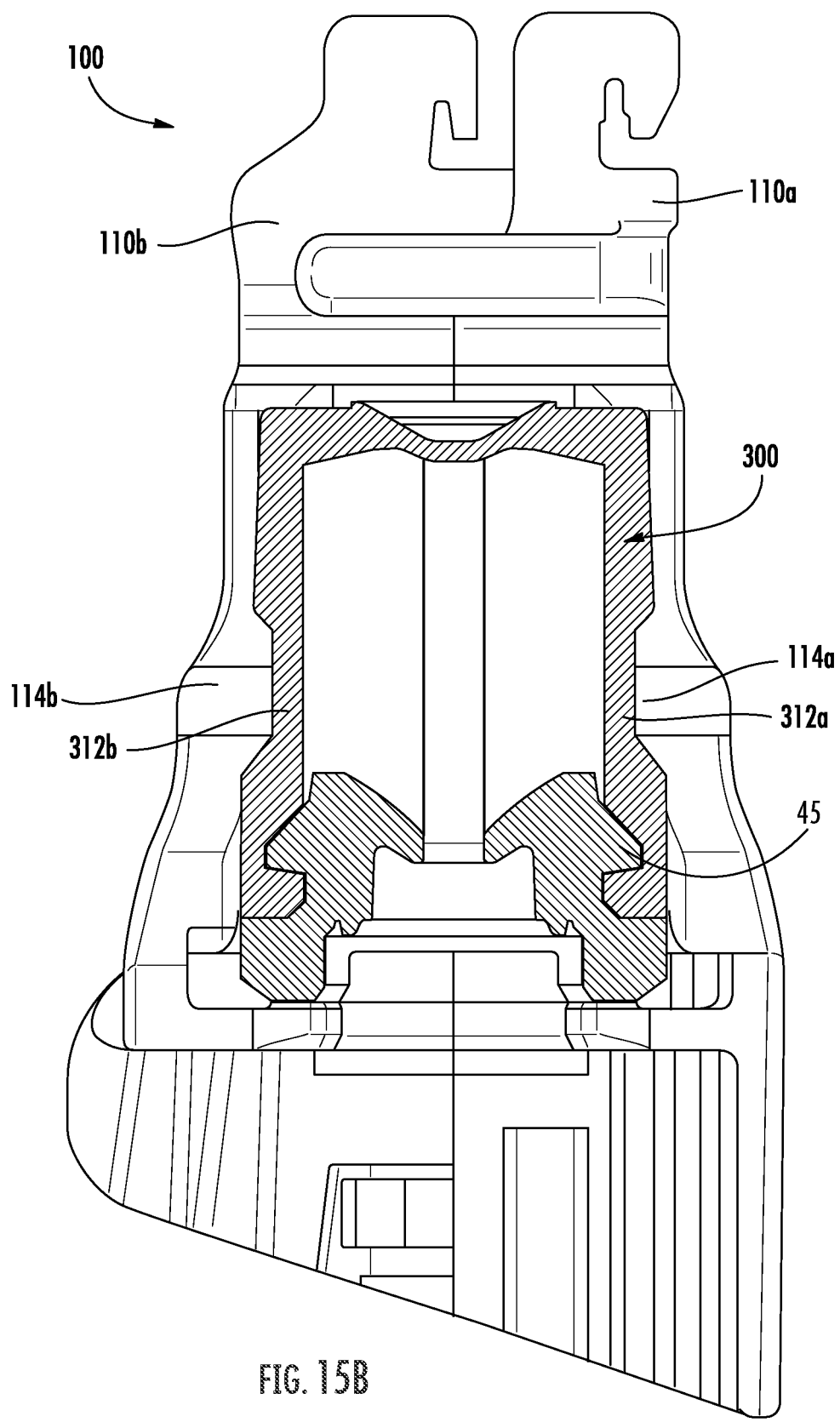

In various embodiments, a variety of advantages may be realized by a biopsy cap housing 20 and/or biopsy cap 300 of the present disclosure. For example, referring to FIG. 15A, in an embodiment, the substantially contiguous lip (e.g., formed by respective lips 117a, 117b of the halves 110a, 110b of the housing 100) extending into the first portion at or near a proximal end of the biopsy cap housing 100 may frictionally and/or compressingly engage a substantially planar top surface of the first surface feature 314a of the biopsy cap 300. In addition, or alternatively, the contiguous wedges on opposite sides of the first portion (e.g., formed by respective wedges 116a, 116b) may frictionally and/or compressingly engage a substantially planar top surface and/or angled side surface of the respective corresponding second and third surface features 314b, 314c of the biopsy cap 300 and a base 45. Referring to FIG. 15B, in addition or alternatively, the elevated surfaces of the first and second pivot members 114a, 114b may frictionally and/or compressingly engage corresponding recessed portions 312a, 312b formed within an outer wall of a biopsy cap 300. These features may be implemented similarly with housing 20 of the embodiment of the endoscope attachment of FIGS. 2-4 and similarly with the base 45, 945 of FIGS. 8, 9, 11, and 12.

In various embodiments, the cumulative effect of these frictional and/or compressive forces along various opposing surfaces and sides of the biopsy cap 300 may limit or prevent axial and/or rotational movement of the biopsy cap 300 within the first portion (upper chamber) of the biopsy cap housing 100 and/or prevent fluid flow (e.g., leakage) around an outer surface of the biopsy cap 300, e.g., during device exchange through a lumen 310 of the biopsy cap 300.

In addition, or as an alternative, to the above-described advantages, a variety of additional advantages may be realized by the interlocking projections and receiving elements of the respective first and second center-split halves 110a, 110b. For example, the interlocking pin(s) 118a/pin hole(s) 118b and snap-lock(s) 120a/snap-lock receiver(s) 120b may provide structural support, minimize movement and equally distribute radially outward forces exerted on the biopsy cap housing 100 across and/or between the first and second center-split halves 110a, 110b. For example, radial outward forces exerted on the biopsy cap housing 100 during exchange of a large (e.g., 16-French) medical instrument through the flexible biopsy cap 300 may be distributed substantially equally along a full length of the biopsy cap housing 100 (e.g., between/along mating surfaces 111a, 111b) rather than concentrated within the upper chamber. In addition, radial outward forces applied unequally to one side of the biopsy cap housing 100, e.g., by a guidewire secured to the first and/or second locking hooks 123a, 123b may be redistributed substantially equally along a full length of the biopsy cap housing 100. In addition, or alternatively, the larger surface area of the interlocking peg(s) 119a/sockets 119b (e.g., as compared to the pin(s) 118a/pinhole(s) 118b) at or near the locking member(s) 124a, 124b may provide additional structural support, minimize movement and equally distribute forces at or near the lower portion of the biopsy cap housing 100, e.g., adjacent to the locking member(s) 124a, 124b which reversibly engage the neck 410 of the endoscope biopsy port 400.

In addition, or as an alternative, to any of the above-described advantages, a variety of additional advantages may be realized by the first and second pivot members 114a, 114b of the respective first and second center-split halves 110a, 110b. For example, in addition to providing an elevated surfaces to frictionally and/or compressingly engage corresponding recessed portions 312a, 312b formed within an outer wall of a biopsy cap 300, the first and second pivot members 114a, 114b may include an increased thickness (e.g., as compared to the remaining wall thickness of the first portions 112a, 112b of the first and second center-split halves 110a, 110b) to provide a strengthened or otherwise fortified section of the biopsy cap housing 100 at a pivot point (e.g., high-stress portion) between the upper and lower chambers. For example, a user may inwardly compress the second portions 122a, 122b of the biopsy cap housing 100 such that the first portions 112a, 112b of the first and second center-split halves 110a, 110b move away from each other and the second portions 122a, 122b of the first and second center-split halves 110a, 110b move towards each other to engage the locking members 124a, 124b of the lower chamber with the neck 610 of the endoscope biopsy port 600 (FIG. 6A). Similarly, a user may inwardly compress the first portions 112a, 112b of the biopsy cap housing 100 such that the first portions 112a, 112b of the center-split halves 110a, 110b move toward each other and the second portions 122a, 122b of the first and second center-split halves 110a, 110b move away from each other to disengage the locking members 124a, 124b from the neck 610 of the endoscope biopsy port 600. In various embodiments, the shape, location and/or thickness of the first and second pivot members 114a, 114b may provide increased strength and/or flexibility as compared to a corresponding pivot point of a biopsy cap housing 100 without increasing the overall amount of material at the first and second pivot members 114a, 114b. These features may be implemented similarly with housing 20 of the embodiment of the endoscope attachment of FIGS. 2-4.

In addition, or as an alternative, to any of the above-described advantages, the ability of the platforms of the stabilizers 128a to prevent over-extension of the locking members 124a, 124b may further prevent or minimize the cumulative effects of wear-and-tear resulting from incremental and persistent over-extension of the locking members 124a, 124b before or following repeated engagement and disengagement with the neck 610 of the endoscope biopsy port 600.

In various embodiments, the first and second center-split halves 110a, 110b, may be integrally formed from (co-molded, co-extruded, injection molded etc.) a variety of high-quality polymers (e.g., acetyl, etc.) which may provide the requisite yield strain and force modulus to withstand the various radial and load forces exerted on the biopsy cap housing while also maintaining sufficient flexibility to be opened or closed using the force applied by a user's fingers. These features may be implemented similarly with housing 20 of the embodiment of the endoscope attachment of FIGS. 2-4.

The present disclosure is not limited to embodiments in which the one or more projections are located exclusively on a mating surface of the first center-split half and the corresponding one or more receiving elements are located exclusively on a mating surface of the second center-split half. In various embodiments, the one or more projections may be located on a mating surface of the second center-split half and the corresponding one or more receiving elements may be located on a mating surface of the first center-split half. In various additional embodiments, the mating surface of the first center-split half may include both projections and receiving elements configured to receive and/or be received within corresponding receiving elements and projections on the mating surface of the second center-split half.

The materials that can be used for the various components of the endoscope attachment 18 (and/or other endoscope attachments disclosed herein) may include those commonly associated with medical instruments. For example, the endoscope attachment 18 may be made from a metal, metal alloy, polymer (some examples of which are disclosed below), a metal-polymer composite, ceramics, combinations thereof, and the like, or other suitable material. Some examples of suitable polymers may include acrylonitrile butadiene styrene, acrylonitrile butadiene styrene and polycarbonate, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-6, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A housing attachment defining an upper chamber configured to receive a biopsy cap and a lower chamber configured to receive a biopsy port of an endoscope, the housing attachment comprising:
    a first housing portion comprising:
        a first portion partially defining the upper chamber and having a proximal end and a distal end;
        a second portion partially defining the lower chamber and having a proximal end adjacent the distal end of the first portion, and a distal end; and
        one or more locking members extending from an inner surface of the first portion at or near the proximal end thereof and configured to engage around a neck of the biopsy port; and
    a second housing portion comprising:
        a first portion partially defining the upper chamber and having a proximal end and a distal end;
        a second portion partially defining the lower chamber and having a proximal end adjacent the distal end of the first portion, and a distal end; and
        one or more locking members extending from an inner surface of the second portion at or near the proximal end thereof and configured to engage around the neck of the biopsy port;
    wherein mating surfaces of the first and second housing portions are configured to interlock.

2. The housing attachment of claim 1, wherein the upper chamber is configured to receive a biopsy cap with a base disposed therein configured to be disposed above the biopsy port, and wherein the lower chamber is configured to receive the biopsy port.

3. The housing attachment of claim 2, wherein the first housing portion and the second housing portion each comprise a substantially radially raised portion configured to engage corresponding recessed portions formed within an outer wall of a biopsy cap.

4. The housing attachment of claim 2, further comprising a base disposed about the biopsy port and disposed within the biopsy cap.

5. The housing attachment of claim 1, further comprising a first locking hook attached to a proximal end of the first housing portion, and a second locking hook attached to a proximal end of the second housing portion, wherein the first and second locking hooks are substantially adjacent to each other when the first and second housing portions are interlocked.

6. The housing attachment of claim 1, wherein one or more of the one or more locking members extending from the first housing portion, and one or more of the one or more locking members extending from the second housing portion are each angled radially inward and toward a direction of the upper chamber.

7. The housing attachment of claim 1, further comprising at least one stabilizing member extending from the inner surface of the first housing portion or the second housing portion, the at least one stabilizing member configured to collide with one or more of the one or more locking members upon a radial deformation of the locking member.

8. The housing attachment of claim 7, wherein the at least one stabilizing member comprises a perpendicular surface that is substantially perpendicular to the radial flexure of at least one of the locking members.

9. The housing attachment of claim 7, wherein the at least one stabilizing member is positioned such that at least one of the one or more locking members may radially deform a maximum of about 15° to about 25°.

10. The housing attachment of claim 1, wherein the upper chamber is dimensioned to engage a biopsy cap positioned therein.

11. A biopsy cap assembly, comprising:
    a biopsy cap having a base; and
    a housing attachment defining an upper chamber configured to receive a biopsy cap and a lower chamber configured to receive a biopsy port of an endoscope, the housing attachment comprising:
        a first housing portion comprising:
            a first portion partially defining an upper chamber dimensioned to engage the biopsy cap therein;
            a second portion partially defining a lower chamber configured to engage a biopsy port of an endoscope; and
            one or more locking members extending from an inner surface of the first portion at or near the proximal end thereof and configured to engage around a neck of the biopsy port; and a second housing portion comprising:
   a first portion partially defining the upper chamber and dimensioned to engage the biopsy cap therein;
   a second portion partially defining the lower chamber; and
   one or more locking members extending from an inner surface of the second portion at or near the proximal end thereof and configured to engage around the neck of the biopsy port;

wherein mating surfaces of the first and second-housing portions are configured to interlock to define the upper and lower chambers.

12. The biopsy cap assembly of claim 11, wherein an outer wall of the biopsy cap includes recessed portions formed therein, and wherein the first housing portion and the second housing portion each comprise a substantially radially raised portion configured to engage corresponding recessed portions formed within an outer wall of a biopsy cap.

13. The biopsy cap assembly of claim 11, wherein the base engages around the neck of the biopsy cap within the upper chamber.

14. The biopsy cap assembly of claim 11, wherein the housing portions include a lip extending into a proximal end of the upper chamber, and the biopsy cap includes a wedge extending outward from a top surface of the cap, and wherein the lip is configured to engage the top surface of the wedge.

15. The biopsy cap assembly of claim 11, wherein the housing includes a wedge formed within the inner surfaces of the first and second portions of the first and second housing portions, and the biopsy cap includes a wedge extending outward from an outer wall of the biopsy cap top, wherein the wedge of the housing is configured to engage the wedge of the biopsy cap.

16. A housing attachment for a biopsy port of an endoscope, the housing attachment comprising:
   a body comprising a first housing portion and a second housing portion, each of the first housing portion and the second housing portion comprising:
      an upper chamber configured to accept and engage a biopsy cap;
      a lower chamber adjacent the upper chamber configured to receive the biopsy port; and
      a skirt region extending from the lower chamber in a direction away from the upper chamber and configured to extend circumferentially around a portion of a handle of the endoscope, the skirt region having a skirt shape set to follow the contour of the portion of the handle of the endoscope, wherein the skirt region is configured to maintain the skirt shape when the skirt region is not attached to the endoscope.

17. The housing attachment of claim 16, wherein the skirt region of at least one of the housing portions comprises internal gripping members along an inner surface of the skirt region configured to frictionally fit with the portion of the endoscope.

18. The housing attachment of claim 16, wherein the upper chamber comprises a substantially radially raised portion configured to engage corresponding recessed portions formed within an outer wall of a biopsy cap.

19. The housing attachment of claim 16, further comprising a grip region about an external surface of the body at the upper chamber of at least one of the housing portions, the grip region comprising external gripping members configured for a user to grasp.

20. The housing attachment of claim 19, further comprising at least two slots extending through the body along the upper chamber and the skirt region of at least one of the housing portions, the at least two slots configured to allow the body to flex upon compressing the grip region.

* * * * *